(12) United States Patent
Potter et al.

(10) Patent No.: US 7,700,117 B2
(45) Date of Patent: Apr. 20, 2010

(54) **CAMP FACTOR OF *STREPTOCOCCUS UBERIS***

(75) Inventors: Andrew A. Potter, Saskatoon (CA); Jose Perez-Casal, Saskatoon (CA); Michael Fontaine, Scotland (GB); Xinming Song, Saskatoon (CA)

(73) Assignee: University of Saskatchewan, Saskatoon, Saskatchewan (CA)

( * ) Notice: Subject to any disclaimer, the term of this patent is extended or adjusted under 35 U.S.C. 154(b) by 354 days.

(21) Appl. No.: 10/864,012

(22) Filed: Jun. 8, 2004

(65) Prior Publication Data

US 2004/0219639 A1  Nov. 4, 2004

Related U.S. Application Data

(60) Division of application No. 10/134,021, filed on Apr. 26, 2002, now Pat. No. 6,936,259, which is a continuation-in-part of application No. 09/234,733, filed on Jan. 21, 1999, now Pat. No. 6,908,619, which is a division of application No. 08/658,277, filed on Jun. 5, 1996, now Pat. No. 5,863,543.

(60) Provisional application No. 60/000,083, filed on Jun. 8, 1995.

(51) Int. Cl.
*A61K 39/00* (2006.01)
*A61K 39/02* (2006.01)
*A61K 39/09* (2006.01)
*A61K 39/38* (2006.01)
*A61K 39/108* (2006.01)
*A61K 45/00* (2006.01)
*A61K 47/00* (2006.01)

(52) U.S. Cl. .............. 424/244.1; 424/184.1; 424/185.1; 424/200.1; 424/234.1; 424/237.1; 424/278.1; 424/282.1; 435/71.1; 435/91.1; 435/91.4; 435/253.4; 435/320.1; 435/455; 435/471; 514/44

(58) Field of Classification Search .............. 424/93.44, 424/175.1, 184.1, 185.1, 190.1, 192.1, 203.1, 424/278.1, 282.1; 435/7.34, 36, 69.1, 71.1; 530/388.4, 403; 536/23.7
See application file for complete search history.

(56) References Cited

U.S. PATENT DOCUMENTS 4,879,213 A   11/1989   Fox et al.

FOREIGN PATENT DOCUMENTS

EP         0 626 452 A1    11/1994

(Continued)

OTHER PUBLICATIONS

Frey et al. 1989. Infection and Immunity. vol. 57 (7): 2050-2056.*

(Continued)

*Primary Examiner*—Mark Navarro
*Assistant Examiner*—JaNa Hines
(74) *Attorney, Agent, or Firm*—Judy Jarecki-Black; Merial Limited; Thomas Kowalski, Esq.

(57) ABSTRACT

The CAMP factor gene of *Streptococcus uberis* (*S. uberis*) is described, as well as the recombinant production of CAMP factor therefrom. Also disclosed are chimeric CAMP factor constructs, including CAMP factor epitopes from more than one bacterial species. The CAMP factors and chimeras including the same can be used in immunogenic compositions for the prevention and treatment of bacterial infections.

14 Claims, 11 Drawing Sheets

FOREIGN PATENT DOCUMENTS

WO    WO 96/41879 A1    12/1996

OTHER PUBLICATIONS

Podielski et al. 1994. Med. Microbiol. Immunol. vol. 183: 239-256.*
Ruhlmann et al. 1988. vol. 235(1,2): 262-266.*
Schneewind et al. 1988. Infection and Immunity. vol. 56(8): 2174-2179.*
Bemheimer et al., "Nature and Mechanism of Action of the Camp Protein of Group B *Streptococci*", *Infection and Immunity* 23(3): 838-844 (1979).
Burgess et al., *J. Cell Biol.* 111: 2129-2138 (1990).
Christie et al., "A Note on a Lytic Phenomenon Shown by Group B *Streptococci*", *Aus. J. Exp. Bio. Med. Sci.* 22: 197-200 (1944).
Fehrenbach et al.; "Interaction of Amphiphilic Bacterial Polypeptides With Artificial Membranes", *Bacterial Protein Tokins*, pp. 317-324 (1984).
Fehrenbach et al., Role of Camp-Factor (Protein B) for Virulence, (eds.) *Bacterial Protein Toxins, Zbl. Bakt. Suppl.* 17: 351-357 (1988).
Finch et al., "Further Studies on the Efficacy of a Live Vaccine Against Mastitis Caused by *Streptococcus uberis*", Vaccine 15(10): 1138-1143, 1997.
Figura et al., "Differentiation of Motile and Mesophilic Aeromonas Strains Into Species by Testing for a Camp0-Like Factor", *J. Clin. Microbiol.* 25(7): 1341-1342 (1987).
Fontaine et al., "Immunisation of Dairy Cattle With Recombinant *Streptococcus uberis* GAPC or a Chimeric Camp Antigen Confers Protection Against Heterologous Bacterial Challenge", Vaccine 20:2278-2286, 2002.
Fontaine et al., "Immunisation of Dairy Cattle With Recombinant *Strptococcus uberis* GAPC or a Chimeric Camp Antigen Confers Protection Against Heterologous Bacterial Challenge", Vaccine 20:3047-3048, 2002.
Fraser, Gordon. "Bacteriology: Haemolytic Activity of corynebacterium", *Nature* 189: 246- (1961).
Frey et al., "Cloning and Expression of a Cohemolysin. The Camp Factor of *Actinobacillus pleuropneumoniae*", Infection & Immunity 57(7): 2050-2056 (1989).
George et al., "Macromol Sequencing Synthesis", *Select Meth. Appl.* Alan Liss Inc. (1988).
Herzog et al., *DNA and Cell Biology*, 12(6): 465-471 (1993).
Jiang et al., "Cloning, Sequencing and Expression of the Camp Factor Gene of *Streptococcus uberis*", 20: 297-307 (1996).
Jurgens et al., "Purification and Characterization of Camp-Factor From *Streptococcus agalactiae* by Hydrophobic Interaction Chromatography and Chromatofocusing", *Journal of Chromatography*. 348: 363-370 (1985).
Jurgens et al., "Unspecific Binding of Group B *Streptococcal cocytolysin* (Camp Factor) to Immunoglobins and its Possible Role in Pathogenicity", *Exp. Med.* 165: 720-732 (1987).
Kohler, W. "Camp-Like Phenomena of Vibrios", *Zentralbl. Bakteriol. Mikrobiol. Hyg. Ser. A* 270: 35-40 (1988).
Lazar et al., *Mol. Cell. Biol.* 8(3): 1247-1252 (1988).
Leigh et al., "Vaccination With the Plasminogen Activator From *Streptococcus uberis* Induces an Inhibitory Response and Protects Against Experimental Infection in the Dairy Cow", Vaccine 17:851-857, 1997.
Levinson et al., *Examination & Board Review, Medical Microbiology & Immunology* pp. 292-293 (1994).
Podbielski, *Med. Microbiol. Immunol.* 183: 239-256 (1994).
Rocourt et al., "Notes; *Listeria welshimeri* SP. Nov. and *Listeria seeligeri* SP. Nov." *International J. Syst. Bacteriol.* 33(4): 866-869 (1983).
Rudinger et al., "Peptide Hormones", *ed. Parsons, University Park Press* (1976).
Ruhlmann et al., "Complete Amino Acid Sequence of Protein B", *Fed. Of Europ. Biochem. Soc.* 235 (1,2): 262-266 (1988).
Sambrook et al., "Expression of Cloned Genes in *E. coli*", *Molecular Cloning, A Laborotory Manual*, Chp. 17, *CSH* (1989).
Schneewind at al., "Cloning and Expression of the Camp Factor of Group B *Streptococci* in *Escherichia coli*", *Infection & Immunity* 56(8): 2174-2179 (1988).
Skalka et al., "Lethal Effect of Camp-Factor and Uberis-Factor-A New Finding About Diffusible Exosubstances of *Streptococcus Agalactiae* and *Streptococcus uberis*", *Zentralbl. Bakteriol. Ser. A* 249: 190-194 (1981).
Sterzik et al., "Interaction of the Camp-Factor From *S. agalactiae* With Artificial Membranes", *Bacterial Protein Toxins*, pp. 195-196 (1984).
Sterzik et al., "Structure and Function of Camp Factor of *Streptococcus agalactiae*", *Zentrnibl. Bakteriol. Mikrobiol. Hyg. Abt. 1*, 15: 101-108 (1985).
Williams, *Lett. Appl. Microbiol.* 12(1): 23-28 (1991).

* cited by examiner

```
  1 ATG CTT ATG GAA TTC AAA AAG TTA CTT TAT TTA ACT GGT TCA ATC
    Met Leu Met Glu Phe Lys Lys Leu Leu Tyr Leu Thr Gly Ser Ile   15

46 GCA GGA ATT ACT TTA TTT TCC CCA ATT TTA ACA AGT GTC CAA GCA
    Ala Gly Ile Thr Leu Phe Ser Pro Ile Leu Thr Ser Val Gln Ala   30

91 AAT CAA ATA AAT GTT AGT CAA CCA TCT AAT AAT GAA AGT AAT GTT
    Asn Gln Ile Asn Val Ser Gln Pro Ser Asn Asn Glu Ser Asn Val   45

136 ATT TCA CAG AAA AAA GAA GAA ATT GAT AAT AGT CTA AAT CAG GAA
    Ile Ser Gln Lys Lys Glu Glu Ile Asp Asn Ser Leu Asn Gln Glu   60

181 AGT GCT CAA CTA TAT GCC TTG AAA GAA GAT GTT AAA GGA ACT GAG
    Ser Ala Gln Leu Tyr Ala Leu Lys Glu Asp Val Lys Gly Thr Glu   75

226 AAA GAA CAA TCA GTT AAT TCA GCA ATT TCA GCT GTT GAA AAT TTA
    Lys Glu Gln Ser Val Asn Ser Ala Ile Ser Ala Val Glu Asn Leu   90

271 AAA ACT TCA CTT AGA GCT AAT CCT GAA ACA ATT TAT GAT TTA AAT
    Lys Thr Ser Leu Arg Ala Asn Pro Glu Thr Ile Tyr Asp Leu Asn  105

316 TCG ATT GGA ACA AGA GTA GAA GCA ATC TCT GAC GTG ATT CAA GCA
    Ser Ile Gly Thr Arg Val Glu Ala Ile Ser Asp Val Ile Gln Ala  120

361 ATT GTT TTT TCA ACG CAA CAG TTA ACA AAT AAA GTT GAT CAA GCT
    Ile Val Phe Ser Thr Gln Gln Leu Thr Asn Lys Val Asp Gln Ala  135

406 CAC ATT GAT ATG GGA TTT GCT ATT ACG AAA TTA CTT ATT CGC ATT
    His Ile Asp Met Gly Phe Ala Ile Thr Lys Leu Leu Ile Arg Ile  150

451 GCA GAC CCA TTT GCT TCA AAT GAA TCC ATT AAA GGG CAA GTC GAA
    Ala Asp Pro Phe Ala Ser Asn Glu Ser Ile Lys Gly Gln Val Glu  165

496 GCT GTT AAA CAA GTG CAA GCG ACT GTG CTT ACC TAT CCC GAT TTG
    Ala Val Lys Gln Val Gln Ala Thr Val Leu Thr Tyr Pro Asp Leu  180

541 CAG CCT ACG GAT AGA GCA ACT ATT TAC GTT AAA TCA AAA TTA GAC
    Gln Pro Thr Asp Arg Ala Thr Ile Tyr Val Lys Ser Lys Leu Asp  195

586 AAG CTT ATT TGG CAA ACA AGA ATT ACC AGA GAT CAA AAA GTT CTT
    Lys Leu Ile Trp Gln Thr Arg Ile Thr Arg Asp Gln Lys Val Leu  210

631 AAT GTA AAG AGT TTT GAA GTT TAT CAT CAA TTA AAT AAA GCT ATC
    Asn Val Lys Ser Phe Glu Val Tyr His Gln Leu Asn Lys Ala Ile  225

676 ACA CAT GCA GTA GGT GTA CAA TTA AAT CCA ACT GTA ACA GTT GCA
    Thr His Ala Val Gly Val Gln Leu Asn Pro Thr Val Thr Val Ala  240

721 CAA GTT GAC CAA GAA ATC AAA GTG CTA CAA GAA GCA TTA AAT ACT
    Gln Val Asp Gln Glu Ile Lys Val Leu Gln Glu Ala Leu Asn Thr  255

766 GCT CTA CAG TAA
    Ala Leu Gln ---                                              258
```

FIG. 2

```
  1  ATG AAC GTT ACA CAT ATG ATG TAT CTA TCT GGA ACT CTA GTG GCT
     Met Asn Val Thr His Met Met Tyr Leu Ser Gly Thr Leu Val Ala   15

46  GGT GCA TTG TTA TTT TCA CCA GCT GTA TTA GAA GTA CAT GCT GAT
     Gly Ala Leu Leu Phe Ser Pro Ala Val Leu Glu Val His Ala Asp   30

91  CAA GTG ACA ACT CCA CAA GTG GTA AAT CAT GTA AAT AGT AAT AAT
     Gln Val Thr Thr Pro Gln Val Val Asn His Val Asn Ser Asn Asn   45

136  CAA GCC CAG CAA ATG GCT CAA AAG CTT GAT CAA GAT AGC ATT CAG
     Gln Ala Gln Gln Met Ala Gln Lys Leu Asp Gln Asp Ser Ile Gln   60

181  TTG AGA AAT ATC AAA GAT AAT GTT CAG GGA ACA GAT TAT GAA AAA
     Leu Arg Asn Ile Lys Asp Asn Val Gln Gly Thr Asp Tyr Glu Lys   75

226  CCG GTT AAT GAG GCT ATT ACT AGC GTG GAA AAA TTA AAG ACT TCA
     Pro Val Asn Glu Ala Ile Thr Ser Val Glu Lys Leu Lys Thr Ser   90

271  TTG CGT GCC AAC CCT GAG ACA GTT TAT GAT TTG AAT TCT ATT GGT
     Leu Arg Ala Asn Pro Glu Thr Val Tyr Asp Leu Asn Ser Ile Gly  105

316  AGT CGT GTA GAA GCC TTA ACA GAT GTG ATT GAA GCA ATC ACT TTT
     Ser Arg Val Glu Ala Leu Thr Asp Val Ile Glu Ala Ile Thr Phe  120

361  TCA ACT CAA CAT TTA ACA AAT AAG GTT AGT CAA GCA AAT ATT GAT
     Ser Thr Gln His Leu Thr Asn Lys Val Ser Gln Ala Asn Ile Asp  135

406  ATG GGA TTT GGG ATA ACT AAG CTA GTT ATT CGC ATT TTA GAT CCA
     Met Gly Phe Gly Ile Thr Lys Leu Val Ile Arg Ile Leu Asp Pro  150

451  TTT GCT TCA GTT GAT TCA ATT AAA GCT CAA GTT AAC GAT GTA AAG
     Phe Ala Ser Val Asp Ser Ile Lys Ala Gln Val Asn Asp Val Lys  165

496  GCA TTA GAA CAA AAA GTT TTA ACT TAT CCT GAT TTA AAA CCA ACT
     Ala Leu Glu Gln Lys Val Leu Thr Tyr Pro Asp Leu Lys Pro Thr  180

541  GAT AGA GCT ACC ATC TAT ACA AAA TCA AAA CTT GAT AAG GAA ATC
     Asp Arg Ala Thr Ile Tyr Thr Lys Ser Lys Leu Asp Lys Glu Ile  195

586  TGG AAT ACA CGC TTT ACT AGA GAT AAA AAA GTA CTT AAC GTC AAA
     Trp Asn Thr Arg Phe Thr Arg Asp Lys Lys Val Leu Asn Val Lys  210

631  GAA TTT AAA GTT TAC AAT ACT TTA AAT AAA GCA ATC ACA CAT GCT
     Glu Phe Lys Val Tyr Asn Thr Leu Asn Lys Ala Ile Thr His Ala  225

676  GTT GGA GTT CAG TTG AAT CCA AAT GTT ACG GTA CAA CAA GTT GAT
     Val Gly Val Gln Leu Asn Pro Asn Val Thr Val Gln Gln Val Asp  240

721  CAA GAG ATT GTA ACA TTA CAA GCA GCA CTT CAA ACA GCA TTA AAA
     Gln Glu Ile Val Thr Leu Gln Ala Ala Leu Gln Thr Ala Leu Lys  255

766  TAA
```

FIG. 3

```
                 1                                              ↓                          50
AgalCAMP  ~~MNVTHMMY  LSGTLVAGAL  LFSPAVLEVH  ADQVTTPQVV  NHVNS..NNQ
UberCAMP  MLMEFKKLLY  LTGS.IAGIT  LFSPILTSVQ  ANQINVSQPS  NNESNVISQK
Consensus --M------Y  L-G---AG--  LFSP----V-  A-Q----Q--  N---------

51                                                                        100
AgalCAMP  AQQMAQKLDQ  DSIQLRNIKD  NVQGTDYEKP  VNEAITSVEK  LKTSLRANPE
UberCAMP  KEEIDNSLNQ  ESAQLYALKE  DVKGTEKEQS  VNSAISAVEN  LKTSLRANPE
Consensus -------L-Q  -S-QL---K-  -V-GT--E--  VN-AI--VE-  LKTSLRANPE 101                                                                        150
AgalCAMP  TVYDLNSIGS  RVEALTDVIE  AITFSTQHLT  NKVSQANIDM  GFGITKLVIR
UberCAMP  TIYDLNSIGT  RVEAISDVIQ  AIVFSTQQLT  NKVDQAHIDM  GFAITKLLIR
Consensus T-YDLNSIG-  RVEA--DVI-  AI-FSTQ-LT  NKV-QA-IDM  GF-ITKL-IR 151                                                                        200
AgalCAMP  ILDPFASVDS  IKAQVNDVKA  LEQKVLTYPD  LKPTDRATIY  TKSKLDKEIW
UberCAMP  IADPFASNES  IKGQVEAVKQ  VQATVLTYPD  LQPTDRATIY  VKSKLDKLIW
Consensus I-DPFAS--S  IK-QV--VK-  ----VLTYPD  L-PTDRATIY  -KSKLDK-IW 201                                                                        250
AgalCAMP  NTRFTRDKKV  LNVKEFKVYN  TLNKAITHAV  GVQLNPNVTV  QQVDQEIVTL
UberCAMP  QTRITRDQKV  LNVKSFEVYH  QLNKAITHAV  GVQLNPTVTV  AQVDQEIKVL
Consensus -TR-TRD-KV  LNVK-F-VY-  -LNKAITHAV  GVQLNP-VTV  -QVDQEI--L 251
AgalCAMP  QAALQTALK
UberCAMP  QEALNTALQ
Consensus Q-AL-TAL-
```

FIG. 4

*S. agalactiae* CAMP protein

MNVTHMMYLSGTLVAGALLFSPAVLEVHA^DQ 31
Score: 10.1
Probability: 1.753E-02
SP length: 29

*S. uberis* CAMP protein

MLMEFKKLLYLTGSIAGITLFSPILTSVQA^NQ 32
Score: 9.3
Probability: 1.605E-02
SP length: 30

FIG. 6

```
  1 ATG AAA AAA ATA ACA GGG ATT ATT TTA TTG CTT CTT GCA GTC ATT ATT CTG TCT GCA TGC
    Met Lys Lys Ile Thr Gly Ile Ile Leu Leu Leu Leu Ala Val Ile Ile Leu Ser Ala Cys  20

61 CAG GCA AAC TAC GGA TCC AAT CAA ATA AAT GTT AGT CAA CCA TCT AAT AAT GAA AGT AAT
    Gln Ala Asn Tyr Gly Ser Asn Gln Ile Asn Val Ser Gln Pro Ser Asn Asn Glu Ser Asn  40

121 GTT ATT TCA CAG AAA AAA GAA GAA ATT GAT AAT AGT CTA AAT CAG GAA AGT GCT CAA CTA
    Val Ile Ser Gln Lys Lys Glu Glu Ile Asp Asn Ser Leu Asn Gln Glu Ser Ala Gln Leu  60

181 TAT GCC TTG AAA GAA GAT GTT AAA GGA ACT GAG AAA GAA CAA TCA GTT AAT TCA GCA ATT
    Tyr Ala Leu Lys Glu Asp Val Lys Gly Thr Glu Lys Glu Gln Ser Val Asn Ser Ala Ile  80

241 TCA GCT GTT GAA AAT CTC GAG CAA GTG ACA ACT CCA CAA GTG GTA AAT CAT GTA AAT AGT
    Ser Ala Val Glu Asn Leu Glu Gln Val Thr Thr Pro Gln Val Val Asn His Val Asn Ser 100

301 AAT AAT CAA GCC CAG CAA ATG GCT CAA AAG CTT GAT CAA GAT AGC ATT CAG TTG AGA AAT
    Asn Asn Gln Ala Gln Gln Met Ala Gln Lys Leu Asp Gln Asp Ser Ile Gln Leu Arg Asn 120

361 ATC AAA GAT AAT GTT CAG GGA ACA GAT TAT GAA AAA CCG GTT AAT GAG GCT ATT ACT AGC
    Ile Lys Asp Asn Val Gln Gly Thr Asp Tyr Glu Lys Pro Val Asn Glu Ala Ile Thr Ser 140

421 GTG GAA AAA TTA AGG GCT AAA ACT TCA CTT AGA GCT AAT CCT GAA ACA ATT TAT GAT TTA
    Val Glu Lys Leu Arg Ala Lys Thr Ser Leu Arg Ala Asn Pro Glu Thr Ile Tyr Asp Leu 160

481 AAT TCG ATT GGA ACA AGA GTA GAA GCA ATC TCT GAC GTG ATT CAA GCA ATT GTT TTT TCA
    Asn Ser Ile Gly Thr Arg Val Glu Ala Ile Ser Asp Val Ile Gln Ala Ile Val Phe Ser 180

541 ACG CAA CAG TTA ACA AAT AAA GTT GAT CAA GCT CAC ATT GAT ATG GGA TTT GCT ATT ACG
    Thr Gln Gln Leu Thr Asn Lys Val Asp Gln Ala His Ile Asp Met Gly Phe Ala Ile Thr 200

601 AAA TTA CTT ATT CGC ATT GCA GAC CCA TTT GCT TCA AAT GAA TCC ATT AAA GGG CAA GTC
    Lys Leu Leu Ile Arg Ile Ala Asp Pro Phe Ala Ser Asn Glu Ser Ile Lys Gly Gln Val 220

661 GAA GCT GTT AAA CAA GTG CAA GCG ACT GTG CTT ACC TAT CCC GAT TTG CAG CCT ACG GAT
    Glu Ala Val Lys Gln Val Gln Ala Thr Val Leu Thr Tyr Pro Asp Leu Gln Pro Thr Asp 240

721 AGA GCA ACT ATT TAC GTT AAA TCA AAA TTA GAC AAG CTT ATT TGG CAA ACA AGA ATT ACC
    Arg Ala Thr Ile Tyr Val Lys Ser Lys Leu Asp Lys Leu Ile Trp Gln Thr Arg Ile Thr 260

781 AGA GAT CAA AAA GTT CTT AAT GTA AAG AGT TTT GAA GTT TAT CAT CAA TTA AAT AAA GCT
    Arg Asp Gln Lys Val Leu Asn Val Lys Ser Phe Glu Val Tyr His Gln Leu Asn Lys Ala 280

841 ATC ACA CAT GCA GTA GGT GTA CAA TTA AAT CCA ACT GTA ACA GTT GCA CAA GTT GAC CAA
    Ile Thr His Ala Val Gly Val Gln Leu Asn Pro Thr Val Thr Val Ala Gln Val Asp Gln 300

901 GAA ATC AAA GTG CTA CAA GAA GCA TTA AAT ACT GCT CTA CAG TAA
    Glu Ile Lys Val Leu Gln Glu Ala Leu Asn Thr Ala Leu Gln --- 314
```

FIG. 8

CAMP FACTOR OF *STREPTOCOCCUS UBERIS*

CROSS-REFERENCE TO RELATED APPLICATION

This application is a divisional of U.S. patent application Ser. No. 10/134,021 filed Apr. 26, 2002, now U.S. Pat. No. 6,936,259, which is a continuation-in-part of U.S. patent application Ser. No. 09/234,733, filed Jan. 21, 1999, now U.S. Pat. No. 6,908,619, which is a divisional of U.S. patent application Ser. No. 08/658,277, filed Jun. 5, 1996, now issued as U.S. Pat. No. 5,863,543, from which applications priority is claimed under 35 USC §120, which is related to provisional patent application Ser. No. 60/000,083, filed Jun. 8, 1995, from which application priority is claimed under 35 USC §119(e)(1), and which applications are incorporated herein by reference in their entireties.

TECHNICAL FIELD

The present invention relates generally to bacterial antigens. More particularly, the present invention pertains to the recombinant production of CAMP factor from *Streptococcus uberis* (*S. uberis*) and the use of CAMP factors in vaccine compositions. The present invention also pertains to the production and use of chimeric CAMP factor constructs, comprising epitopes of CAMP factors from more than one bacterial species.

BACKGROUND

*S. uberis* is an important cause of mastitis in dairy cattle and is responsible for about 20% of all clinical cases of mastitis (Bramley, A. J. and Dodd, F. H. (1984) *J. Dairy Res.* 51:481-512; Bramley, A. J. (1987) *Animal Health Nutrition* 42:12-16; Watts, J. L. (1988) *J. Dairy Sci.* 71:1616-1624). Since antimicrobial treatment is generally ineffective in treating *S. uberis* mastitis, the development of control measures must be based on an understanding of virulence factors and protective antigens involved in invasion and protection of the mammary gland (Collins et al. (1988) *J. Dairy Res.* 55:25-32; Leigh et al. (1990) *Res. Vet. Sci.* 49:85-87; Marshall et al. (1986) *J. Dairy Res.* 53: 507-514).

It is known that some *S. uberis* strains can produce hyaluronic acid capsule (Hill, A. W. (1988) *Res. Vet. Sci.* 45:400-404), hyaluronidase (Schaufuss et al. (1989) *Zentralb. Bakteriol. Ser. A* 271:46-53), R-like protein (Groschup, M. H. and Timoney, J. F. (1993) *Res. Vet. Sci.* 54:124-126), and a cohemolysin, the CAMP factor, also known as *UBERIS* factor (Skalka, B. and Smola, J. (1981) *Zentralb. Bakteriol. Ser. A* 249:190-194). However, very little is known of their roles in pathogenicity.

The effect of CAMP factor was first described by Christie et al. in 1944 (Christie et al. (1944) *Aus. J. Exp. Biol. Med. Sci.* 22:197-200). These authors found that group B streptococci (GBS), such as *S. agalactiae*, produced a distinct zone of complete hemolysis when grown near the diffusion zone of the *Staphylococcus aureus* beta-toxin, sphingomyelinase. This phenomenon was called CAMP reaction and the compound for this reaction was characterized as the CAMP factor, an extracellular protein with a molecular weight of 23,500 (Bernheimer et al. (1979) *Infect. Immun.* 23:838-844). The CAMP factor was subsequently purified from *S. agalactiae* and characterized as a 25,000 Da protein with a pI of 8.9 (Jürgens et al. (1985) *J. Chrom.* 348:363-370). The amino acid sequence of *S. agalactiae* CAMP factor was determined by Rühlmann et al. (Rühlmann et al. (1988) *FEBS Lett* 235: 262-266).

The mechanism of the CAMP reaction has been described. See, e.g., Bernheimer et al. (1979) *Infect. Immun.* 23:838-844; Sterzik et al. "Interaction of the CAMP factor from *S. agalactiae* with artificial membranes." In: Alouf et al., eds. *Bacterial protein toxins*, London: Academic Press Inc, 1984; 195-196; Sterzik et al. (1985) *Zentralbl. Bakteriol. Mikrobiol. Hyg. Abt.* 1 *Suppl.* 15:101-108; Fehrenbach et al. "Role of CAMP-factor (protein B) for virulence." In: Fehrenbach et al., eds. *Bacterial protein toxins*, Stuttgart: Gustav Fischer Verlag, 1988; 351-357; Fehrenbach et al. "Interaction of amphiphilic bacterial polypeptides with artificial membranes." In: Alouf et al., eds. *Bacterial protein toxins*, London: Academic Press Inc., 1984:317-324.

CAMP factor has lytic action on a variety of target cells including sheep and bovine erythrocytes, as well as on artificial membranes in which membrane phospholipids and sphingomyelin have been hydrolyzed by phospholipase or sphingomyelinase.

The role of CAMP factor in pathogenicity is unclear. A partially purified CAMP factor from *S. agalactiae* has been shown to be lethal to rabbits when injected intravenously (Skalka, B. and Smola, J. (1981) *Zentralbl. Bakteriol. Ser. A* 249:190-194). Furthermore, intraperitoneal injection of purified CAMP factor into mice has been shown to significantly raise the pathogenicity of a sublethal dose of group B streptococci (Fehrenbach et al. "Role of CAMP-factor (protein B) for virulence." In: Fehrenbach et al., eds. *Bacterial protein toxins*, Stuttgart: Gustav Fischer Verlag, 1988; 351-357). Additionally, like protein A of *S. aureus*, GBS CAMP factor can bind the Fc sites of immunoglobulins and has therefore been designated protein B (Jürgens et al. (1987) *J. Exp. Med.* 165:720-732).

In addition to GBS and *S. uberis*, other bacteria, including *Listeria monocytogenes* and *Listeria seeligeri* (Rocourt, J. and Grimont, P. A. D. (1983) *Int. J. Syst. Bacteriol.* 33:866-869) *Aeromonas* sp. (Figura, N. and Guglielmetti, P. (1987) *J. Clin. Microbiol.* 25:1341-1342), *Rhodococcus equi* (Fraser, G. (1961) *Nature* 189:246), and certain *Vibrio* spp. (Kohler, W. (1988) *Zentralbl. Bakteriol. Mikrobiol. Hyg. Ser. A* 270: 35-40) produce reactions similar to the CAMP effect.

The CAMP factor genes of GBS and *A. pleuropneumoniae* have been cloned and expressed in *Escherichia coli* (Schneewind et al. (1988) *Infect. Immun.* 56:2174-2179; Frey et al. (1989) *Infect. Immun.* 57:2050-2056). Additionally, the gene encoding the CAMP factor from a group A streptococci (GAS) strain, *S. pyogenes*, has also been isolated (Gase et al. (1999) *Infect. Immun.* 67:4725-4731). The CAMP protein products were of similar size and possessed homology to the CAMP proteins of *S. agalactiae* and *S. uberis*. Antibodies raised against the cloned CAMP protein of *A. pleuropneumoniae* neutralized the CAMP reaction mediated by the *E. coli* strain containing the cloned CAMP gene as well as that of *A. pleuropneumoniae*, and also cross-reacted with the *S. agalactiae* CAMP factor. In the GAS strains, the distribution of the cfa (CAMP) gene was analyzed. This gene was widely spread among GAS: 82 of 100 clinical GAS isolates produced a positive CAMP reaction. Of the CAMP-negative strains, 17 of the 18 GAS strains contained the cfa gene. Additionally, CAMP activity was detected in streptococci from serogroups C, M, P, R, and U (Gase et al. (1999) *Infect. Immun.* 67:4725-4731).

However, prior to the present inventors' discovery, the CAMP factor gene of *S. uberis* had not been cloned. Furthermore, the protective capability of CAMP factor had not been previously studied. Additionally, the production and use of chimeric CAMP factor constructs, containing epitopes derived from CAMP factors from more than one microbe, has not previously been described.

DISCLOSURE OF THE INVENTION

The present invention is based on the discovery of the CAMP factor gene of *S. uberis*, as well as the discovery that the CAMP factor, and chimeric constructs including multiple CAMP factor epitopes, is able to protect vertebrate subjects from infection. The CAMP factor, active immunogenic fragments thereof, active analogs thereof, or chimeric proteins including multiple CAMP factors from more than one organism, can be used, either alone or in combination with other antigens, in novel subunit vaccines to provide protection from bacterial infection in vertebrate subjects, or as diagnostic reagents.

Accordingly, in one embodiment, the subject invention is directed to an immunogenic polypeptide comprising one or more CAMP factor epitopes from more than one bacterial species. In certain embodiments, the one or more CAMP factor epitopes are separated by a spacer consisting of 1-20 amino acids. Moreover, the one or more CAMP factor epitopes may be from more than one bacterial species of the genus *Streptococcus*, such as one selected from the group consisting of *S. uberis, S. agalactiae* and *S. pyogenes*.

In additional embodiments, at least one of the CAMP factor epitopes is from the CAMP factor N-terminal variable region corresponding to the region defined by amino acids 1-90 of FIG. 2. In certain embodiments, the epitope is interposed within a CAMP factor protein having at least 80% sequence identity to the CAMP factor protein of FIG. 2 or FIG. 3, and the CAMP factor protein is from a different *streptococcal* species than the CAMP factor epitope from the N-terminal variable region. In particular embodiments, the CAMP factor epitope from the N-terminal variable region comprises a sequence of amino acids having at least 80% sequence identity to the sequence of amino acids depicted at positions 31-87 of FIG. 3 and the CAMP factor protein has at least 80% sequence identity to the CAMP factor protein of FIG. 2.

In other embodiments, the immunogenic polypeptide comprises a sequence of amino acids having at least 80% sequence identity to the contiguous sequence of amino acids depicted at positions 27-314 of FIG. 8, with or without a signal sequence. In yet another embodiment, the immunogenic polypeptide comprises the amino acid sequence depicted in FIG. 8.

In another embodiment, the invention is directed to immunogenic compositions comprising an immunogenic protein as detailed above, and a pharmaceutically acceptable. The composition can additionally comprise an adjuvant.

In further embodiments, the invention is directed to a method of producing an immunogenic composition comprising the steps of:

(1) providing an immunogenic polypeptide as described above; and (2) combining said polypeptide with a pharmaceutically acceptable vehicle.

In additional embodiments, the invention is directed to a method of treating or preventing a bacterial infection in a vertebrate subject comprising administering to the subject a therapeutically effective amount of an immunogenic composition as detailed above. In certain embodiments, the infection is a *streptococcal* infection and causes mastitis.

In yet further embodiments, the invention pertains to antibodies directed against the immunogenic polypeptides described above. The antibodies can be polyclonal or monoclonal.

In additional embodiments, the invention is directed to a polynucleotide comprising a coding sequence encoding an immunogenic polypeptide as described above, a recombinant vector comprising the polynucleotide and at least one control element operably linked to polynucleotide, whereby the coding sequence can be transcribed and translated in a host cell, a host cell comprising the recombinant vector, and a method for producing an immunogenic polypeptide, the method comprising culturing a population of host cells as described above under conditions for producing said polypeptide.

In other embodiments, the invention is directed to a method of detecting *Streptococcus* antibodies in a biological sample, comprising:

(a) reacting the biological sample with the immunogenic polypeptide as described above, under conditions which allow *Streptococcus* antibodies, when present in the biological sample, to bind to the polypeptide to form an antibody/antigen complex; and (b) detecting the presence or absence of the complex, and thereby detecting the presence or absence of *Streptococcus* antibodies in the sample.

In yet other embodiments, the invention is directed to an immunodiagnostic test kit for detecting *Streptococcus* infection, the test kit comprising an immunogenic polypeptide as described above and instructions for conducting the immunodiagnostic test.

These and other embodiments of the present invention will readily occur to those of ordinary skill in the art in view of the disclosure herein.

BRIEF DESCRIPTION OF THE FIGURES

FIG. 2 (SEQ ID NOS:1 and 2) shows the nucleotide sequence and the corresponding amino acid sequence of the *S. uberis* CAMP factor. The nucleotide positions are indicated on the left while amino acid positions are denoted on the right. A signal peptide occurs at amino acids 1-30 of the figure and the mature peptide is represented by amino acid positions 31-258.

FIG. 3 shows (SEQ ID NOS:3 and 4) shows the nucleotide sequence and the corresponding amino acid sequence of the *S. agalactiae* CAMP factor. The nucleotide positions are indicated on the left while amino acid positions are denoted on the right. A signal peptide occurs at amino acids 1-29 of the figure and mature peptide is represented by amino acid positions 30-255.

FIG. 4 shows the homology between *S. agalactiae* (SEQ ID NO:4) and *S. uberis* (SEQ ID NO:2) CAMP proteins. A consensus sequence (SEQ ID NO:5) is also shown. Alignment of the published sequences of the *S. agalactiae* (Agal-CAMP) and *S. uberis* (UberCAMP) CAMP proteins were generated with PileUp, and displayed with Pretty software (a component of the GCG Wisconsin Package, version 10, provided by the SeqWeb sequence analysis package, version 1.1, of the Canadian Bioinformatics Resource). The consensus sequence is shown below the aligned proteins. The residues are numbered on top. The wavy lines indicate spaces added by the algorithm to correct for different size-proteins. The dots depict gaps between the aligned sequences. The dashes in the consensus sequences represent non-identical residues. The parameters used for the alignment were: Comparison table: blosum62; Gap weight: 8 and Gap length weight: 2. The start of the mature sequence is indicated with an arrow. The aligned sequences show approximately 69% sequence similarity and 63% sequence identity. Amino acid residues 1-30 of the *S. uberis* sequence shown in the figure represent the signal sequence while amino acid residues 1-29 of the *S. agalactiae* sequence represent the signal sequence.

FIG. 6 shows the putative signal sequence of *S. agalactiae* CAMP factor (FIG. 6A; SEQ ID NO:6) and *S. uberis* CAMP factor (FIG. 6B; SEQ ID NO:7). The predicted Signal Peptidase I cleavage sites (Indicated by ^) of the *S. agalactiae* and *S. uberis* CAMP proteins are shown. Also shown are the probability score and the length of the signal peptide for each of the two CAMP proteins. The sequences were analyzed by the SPScan algorithm of the GCG software package.

FIG. 8 depicts the nucleotide and amino acid sequences of the LipoF:CAMP3 chimera (SEQ ID NOS:8 and 9). The nucleotide and protein sequence of the CAMP-3 chimera fused to the LipoF signal sequence is shown. The nucleotides are numbered on the left of the figure, while the amino acid residues are numbered on the right. The underlined sequence represents the LipoF signal sequence. The spacer amino acids occur at positions 87, 145 and 146.

DETAILED DESCRIPTION

Figure 1:
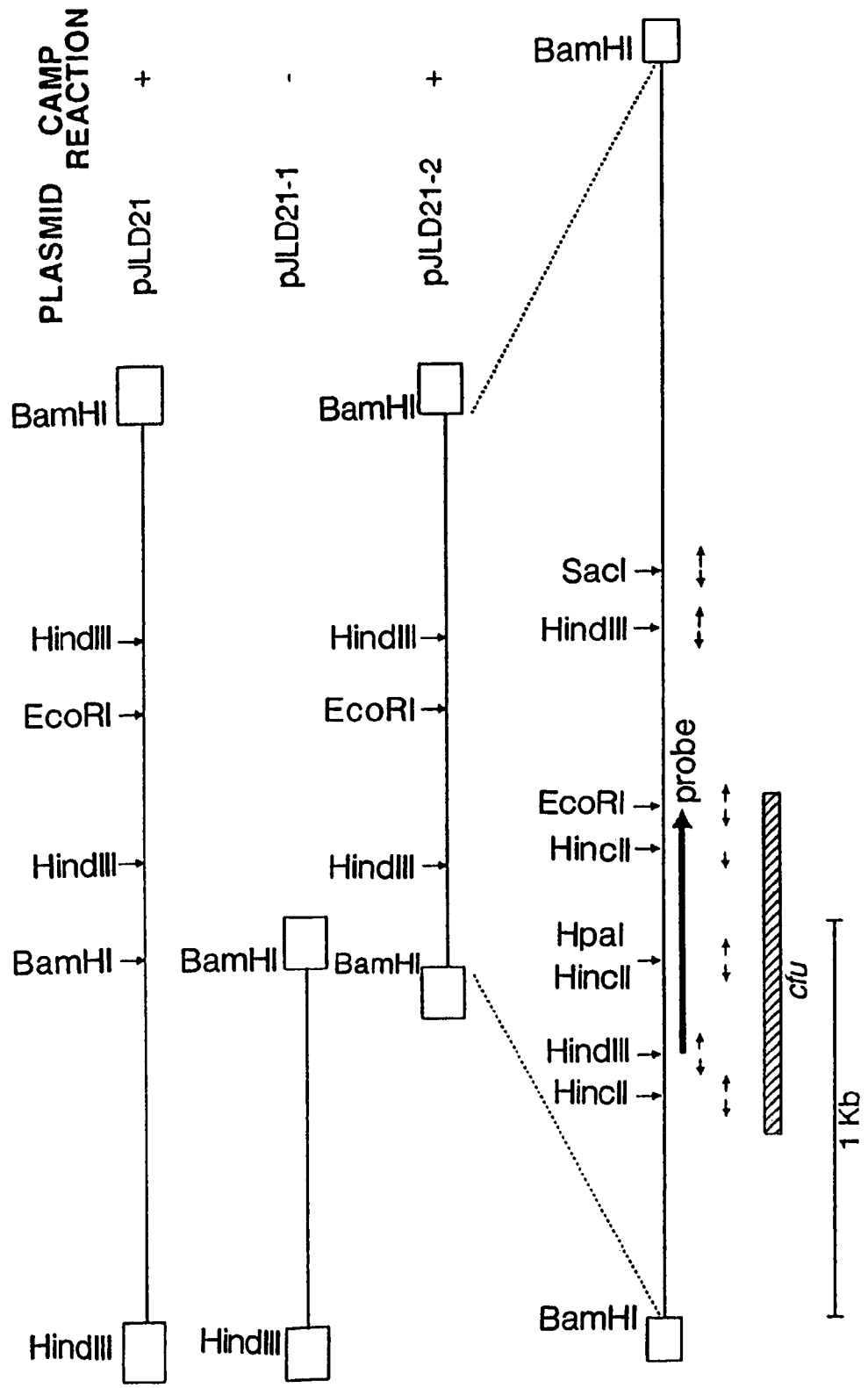
FIG. 1 depicts restriction enzyme maps of recombinant plasmid pJLD21 and subclones thereof, designated pJLD21-1 and pJLD21-2. Lines indicate *S. uberis* insert DNA, while boxes represent the multiple cloning sites of vector pTZ18R. The CAMP activities of recombinant plasmid pJLD21 and its derived subclones are indicated on the right (+, CAMP reaction positive; –, CAMP reaction negative). The small horizontal arrows represent start points and directions of sequencing experiments. The probe fragment used for Southern blot experiments is indicated by the large arrow. The bar at the bottom indicates the location of the open reading frame of CAMP factor gene of *S. uberis* (cfu).

The practice of the present invention will employ, unless otherwise indicated, conventional techniques of molecular biology, microbiology, virology, recombinant DNA technology, and immunology, which are within the skill of the art. Such techniques are explained fully in the literature. See, e.g., Sambrook, Fritsch & Maniatis, *Molecular Cloning: A Laboratory Manual*, Second Edition (1989); *DNA Cloning*, Vols. I and II (D. N. Glover ed. 1985); *Oligonucleotide Synthesis* (M. J. Gait ed. 1984); Nucleic Acid Hybridization (B. D. Hames & S. J. Higgins eds. 1984); *Animal Cell Culture* (R. K. Freshney ed. 1986); *Immobilized Cells and Enzymes* (IRL press, 1986); Perbal, B., *A Practical Guide to Molecular Cloning* (1984); the series, *Methods In Enzymology* (S. Colowick and N. Kaplan eds., Academic Press, Inc.); and *Handbook of Experimental Immunology*, Vols. I-IV (D. M. Weir and C. C. Blackwell eds., 1986, Blackwell Scientific Publications).

All publications, patents and patent applications cited herein, whether supra or infra, are hereby incorporated by reference in their entirety.

The following amino acid abbreviations are used throughout the text:

Alanine: Ala (A) Arginine: Arg (R)
Asparagine: Asn (N) Aspartic acid: Asp (D)
Cysteine: Cys (C) Glutamine: Gln (O)
Glutamic acid: Glu (E) Glycine: Gly (G)
Histidine: His (H) Isoleucine: Ile (I)
Leucine: Leu (L) Lysine: Lys (K)
Methionine: Met (M) Phenylalanine: Phe (F)
Proline: Pro (P) Serine: Ser (S)
Threonine: Thr (T) Tryptophan: Trp (W)
Tyrosine: Tyr (Y) Valine: Val (V)

A. Definitions

In describing the present invention, the following terms will be employed, and are intended to be defined as indicated below.

It must be noted that, as used in this specification and the appended claims, the singular forms "a", "an" and "the" include plural referents unless the content clearly dictates otherwise. Thus, for example, reference to "a CAMP factor" includes a mixture of two or more CAMP factors, and the like.

The term "CAMP factor" or a nucleotide sequence encoding the same, intends a protein or a nucleotide sequence, respectively, which is derived from a CAMP factor gene found in a variety of bacterial species, including, without limitation *Streptococcus uberis*, group B streptococci (GBS) such as *S. agalactiae* (Jürgens et al. (1985) *J. Chromatogr.* 348:363-370; Rühlmann et al. (1988) *FEBS Lett* 235:262-266; Schneewind et al. (1988) *Infect. Immun.* 56:2174-2179), *A. pleuropneumoniae* (Frey et al. (1989) *Infect. Immun.* 57:2050-2056), group A streptococci (GAS), such as *S. pyogenes* (Gase et al. (1999) *Infect. Immun.* 67:4725-4731), and streptococci from serogroups C, M, P, R, and U, *Listeria monocytogenes* and *Listeria seeligeri* (Rocourt, J. and Grimont, P. A. D. (1983) *Int. J. Syst. Bacteriol.* 33:866-869), *Aeromonas* sp. (Figura, N. and Guglielmetti, P. (1987) *J. Clin. Microbiol.* 25:1341-1342), *Rhodococcus equi* (Fraser, G. (1961) *Nature* 189:246), and certain *Vibrio* spp. (Kohler, W. (1988) *Zentralbl. Bakteriol. Mikrobiol. Hyg. Ser. A* 270:35-40).

A representative CAMP factor gene, derived from *S. uberis*, is found in plasmid pJLD21 (ATCC Accession No. 69837). The nucleotide sequence and corresponding amino acid sequence for the *S. uberis* CAMP factor is depicted in FIG. 2 (SEQ ID NOS:1 and 2). FIG. 3 (SEQ ID NOS:3 and 4) shows a nucleotide sequence and corresponding amino acid sequence for the *S. agalactiae* CAMP factor. The sequences for other CAMP factors are known and described in the art as detailed above.

However, a CAMP factor, as defined herein is not limited to the depicted and described sequences as subtypes of each of these bacterial species are known and variations in CAMP proteins will occur between them. Moreover, the derived protein or nucleotide sequences need not be physically derived from the gene described above, but may be generated in any manner, including for example, chemical synthesis, isolation (e.g., from an organism that produces the CAMP factor) or by recombinant production, based on the information provided herein.

The term also includes proteins possessing, as well as lacking, a signal sequence, if such is present. As shown in FIGS. 2, 3 and 4, *S. uberis* and *S. agalactiae* both include signal sequences occurring at amino acid positions 1-30 and 1-29, respectively. In general, the term "mature" CAMP factor refers to a CAMP factor lacking the signal sequence. Thus, the term "mature" CAMP factor with reference to the sequences depicted in FIGS. 2 and 3, refers to the amino acid sequence shown at positions 31-258 of FIG. 2 and positions 30-255 of FIG. 3. The term CAMP factor also refers to proteins in neutral form or in the form of basic or acid addition salts depending on the mode of preparation. Such acid addition salts may involve free amino groups and basic salts may be formed with free carboxyls. Pharmaceutically acceptable basic and acid addition salts are discussed further below. In addition, the proteins may be modified by combination with other biological materials such as lipids (both those occurring naturally with the molecule or other lipids that do not destroy immunological activity) and saccharides, or by side chain modification, such as acetylation of amino groups, phosphorylation of hydroxyl side chains, oxidation of sulfhydryl groups, glycosylation of amino acid residues, as well as other modifications of the encoded primary sequence.

The term "*streptococcal* CAMP factor" intends a CAMP factor, as defined above, derived from a *streptococcal* species that produces the same, including, without limitation, *S. uberis*, GBS such as *S. agalactiae*, GAS, such as *S. pyogenes*, and streptococci from serogroups C, M, P, R, and U. For example, an "*S. uberis* CAMP factor" is a CAMP factor as defined above, derived from *S. uberis*. An "*S. agalactiae* CAMP factor" is a CAMP factor as defined above, derived from *S. agalactiae*.

The terms "variant" and "mutein" of a CAMP factor protein refer to biologically active derivatives of a CAMP factor, as defined above, or fragments of such derivatives, that retain immunological activity as defined herein. The term "mutein" refers to peptides having one or more peptide mimics ("peptoids"), such as those described in International Publication No. WO 91/04282. Preferably, the variant or mutein has at least the same activity as the native molecule. Methods for making polypeptide variants and muteins are known in the art and are described further below.

In general, the term "variant" refers to compounds having a native polypeptide sequence and structure with one or more amino acid additions, substitutions (generally conservative in nature) and/or deletions, relative to the native molecule, so long as the modifications do not destroy activity. Thus, a "variant" of a CAMP factor protein includes a protein with amino acid sequences substantially homologous (as defined below) to contiguous amino acid sequences encoded by the CAMP factor genes, which display immunological activity. Particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cystine, serine threonine, tyrosine. Phenylalanine, tryptophan, and tyrosine are sometimes classified as aromatic amino acids. For example, it is reasonably predictable that an isolated replacement of leucine with isoleucine or valine, or vice versa; an aspartate with a glutamate or vice versa; a threonine with a serine or vice versa; or a similar conservative replacement of an amino acid with a structurally related amino acid, will not have a major effect on the biological activity. Proteins having substantially the same amino acid sequence as the reference molecule, but possessing minor amino acid substitutions that do not substantially affect the immunogenicity of the protein, are therefore within the definition of the reference polypeptide.

Other substitutions include substitutions of naturally occurring amino acids with amino acid analogs. Such amino acid analogs are well known and include, but are not limited to, 2-aminoadipic acid, 3-aminoadipic acid, beta-alanine, beta-aminopropionic acid, 2-aminobutyric acid, 4-aminobutyric acid, piperidinic acid, 6-aminocaproic acid, 2-aminoheptanoic acid, 2-aminoisobutyric acid, 3-aminoisobutyric acid, 2-aminopimelic acid, 2,4-diaminobutyric acid, desmosine, 2,2'-diaminopimelic acid, 2,3-diaminopropionic acid, N-ethylglycine, N-ethylasparagine, hydroxylysine, allo-hydroxylysine, 3-hydroxyproline, 4-hydroxyproline, isodesmosine, allo-isoleucine, N-methylglycine, sarcosine, N-methylisoleucine, 6-N-methyllysine, N-methylvaline, norvaline, norleucine and ornithine.

For example, the polypeptide of interest may include up to about 5-10 conservative or non-conservative amino acid substitutions, or even up to about 15-25 or 20-50 conservative or non-conservative amino acid substitutions, or any integer between these values, so long as the desired function of the molecule remains intact.

By "fragment" is intended a polypeptide or polynucleotide consisting of only a part of the intact polypeptide sequence and structure, or the nucleotide sequence and structure, of the reference gene. The polypeptide fragment can include a C-terminal deletion and/or N-terminal deletion of the native polypeptide, or can be derived from an internal portion of the molecule. Similarly, a polynucleotide fragment can include a 3' and/or a 5' deletion of the native polynucleotide, or can be derived from an internal portion of the molecule. A polypeptide "fragment" of a CAMP factor will generally include at least about 2-5 contiguous amino acid residues, preferably at least about 10 contiguous amino acid residues of the full-length molecule, preferably at least about 15-25 contiguous amino acid residues of the full-length molecule, and most preferably at least about 20-50 or more contiguous amino acid residues of full-length molecule, or any integer between 2 amino acids and the full-length sequence, provided that the fragment in question retains desired activity.

A nucleotide fragment of the gene of interest generally includes at least about 8 contiguous base pairs, more preferably at least about 10-20 contiguous base pairs, and most preferably at least about 25-50, or more, contiguous base pairs of the gene, or any integers between these values. Such fragments are useful as probes and in diagnostic methods, discussed more fully below.

By "mastitis" is meant an inflammation of the mammary gland in mammals, including in cows, ewes, goats, sows, mares, and the like, caused by various bacteria that produce CAMP factors, described more fully below. The infection manifests itself by the infiltration of phagocytic cells in the gland. Generally, 4 clinical types of mastitis are recognized: (1) peracute, associated with swelling, heat, pain, and abnormal secretion in the gland and accompanied by fever and other signs of systemic disturbance, such as marked depression, rapid weak pulse, sunken eyes, weakness and complete anorexia; (2) acute, with changes in the gland similar to those above but where fever, anorexia and depression are slight to moderate; (3) subacute, where no systemic changes are displayed and the changes in the gland and its secretion are less marked: and (4) subclinical, where the inflammatory reaction is detectable only by standard tests for mastitis.

Standard tests for the detection of mastitis include but are not limited to, the California Mastitis Test, the Wisconsin Mastitis Test, the Nagase test, the electronic cell count and somatic cell counts used to detect a persistently high white blood cell content in milk. In general, a somatic cell count of about 300,000 to about 500,000 cells per ml or higher, in milk will indicate the presence of infection. Thus, a vaccine is considered effective in the treatment and/or prevention of mastitis when, for example, the somatic cell count in milk is retained below about 500,000 cells per ml. For a discussion of mastitis and the diagnosis thereof, see, e.g., *The Merck Veterinary Manual. A Handbook of Diagnosis, Therapy, and Disease Prevention and Control for the Veterinarian*, Merck and Co., Rahway, N. J., 1991.

The term "epitope" refers to the site on an antigen or hapten to which specific B cells and T cells respond. The term is also used interchangeably with "antigenic determinant" or "antigenic determinant site." Antibodies that recognize the same epitope can be identified in a simple immunoassay showing the ability of one antibody to block the binding of another antibody to a target antigen.

An "immunological response" to a composition or vaccine is the development in the host of a cellular and/or antibody-mediated immune response to the composition or vaccine of interest. Usually, an "immunological response" includes but is not limited to one or more of the following effects: the production of antibodies, B cells, helper T cells, suppressor T cells, and/or cytotoxic T cells and/or γδ T cells, directed specifically to an antigen or antigens included in the composition or vaccine of interest. Preferably, the host will display a protective immunological response to the CAMP factor in question, e.g., the host will be protected from subsequent infection by the pathogen and such protection will be demonstrated by either a reduction or lack of symptoms normally displayed by an infected host or a quicker recovery time.

The terms "immunogenic" protein or polypeptide refer to an amino acid sequence which elicits an immunological response as described above. An "immunogenic" protein or polypeptide, as used herein, includes the full-length sequence of the CAMP factor in question, including the precursor and mature forms, analogs thereof, or immunogenic fragments thereof.

By "immunogenic fragment" is meant a fragment of a CAMP factor which includes one or more epitopes and thus elicits the immunological response described above. Such fragments can be identified using any number of epitope mapping techniques, well known in the art. See, e.g., *Epitope Mapping Protocols* in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708, 871; Geysen et al. (1984) *Proc. Natl. Acad. Sci. USA* 81:3998-4002; Geysen et al. (1986) *Molec. Immunol.* 23:709-715, all incorporated herein by reference in their entireties. Similarly, conformational epitopes are readily identified by determining spatial conformation of amino acids such as by, e.g., x-ray crystallography and 2-dimensional nuclear magnetic resonance. See, e.g., *Epitope Mapping Protocols*, supra. Antigenic regions of proteins can also be identified using standard antigenicity and hydropathy plots, such as those calculated using, e.g., the Omiga version 1.0 software program available from the Oxford Molecular Group. This computer program employs the Hopp/Woods method, Hopp et al., *Proc. Natl. Acad. Sci USA* (1981) 78:3824-3828 for determining antigenicity profiles, and the Kyte-Doolittle technique, Kyte et al., *J. Mol. Biol*. (1982) 157:105-132 for hydropathy plots.

Immunogenic fragments, for purposes of the present invention, will usually be at least about 2 amino acids in length, more preferably about 5 amino acids in length, and most preferably at least about 10 to 15 amino acids in length. There is no critical upper limit to the length of the fragment, which could comprise nearly the full-length of the protein sequence, or even a fusion protein comprising two or more epitopes of the CAMP factor or factors in question.

An "immunogenic composition" is a composition that comprises an antigenic molecule where administration of the composition to a subject results in the development in the subject of a humoral and/or a cellular immune response to the antigenic molecule of interest.

By "subunit vaccine composition" is meant a composition containing at least one immunogenic polypeptide, but not all antigens, derived from or homologous to an antigen from a pathogen of interest. Such a composition is substantially free of intact pathogen cells or particles, or the lysate of such cells or particles. Thus, a "subunit vaccine composition" is prepared from at least partially purified (preferably substantially purified) immunogenic polypeptides from the pathogen, or recombinant analogs thereof. A subunit vaccine composition can comprise the subunit antigen or antigens of interest substantially free of other antigens or polypeptides from the pathogen.

By "pharmaceutically acceptable" or "pharmacologically acceptable" is meant a material which is not biologically or otherwise undesirable, i.e., the material may be administered to an individual in a formulation or composition without causing any undesirable biological effects or interacting in a deleterious manner with any of the components of the composition in which it is contained.

The term "multiple epitope" protein or polypeptide specifies a sequence of amino acids comprising an epitope as defined herein, which contains at least one epitope repeated two or more times within a linear molecule. The repeating sequence need not be directly connected to itself, is not repeated in nature in the same manner and, further, may be present within a larger sequence which includes other amino acids that are not repeated. For the purposes of this invention, the epitope sequence may either be an exact copy of a wild-type epitope sequence, or a sequence which is "functionally equivalent" as defined herein.

A "fusion" or "chimeric" protein or polypeptide is one in which amino acid sequences from more than one source are joined. Such molecules may be produced synthetically or recombinantly, as described further herein. A representative chimeric protein comprising the mature CAMP protein of *S. uberis* as a backbone, and an N-terminal peptide from the *S. agalactiae* CAMP protein from a region with low homology to the *S. uberis* CAMP product, is shown at amino acid positions 27-314 of FIG. 8. Spacer sequences occur at positions 87, 145 and 146. The CAMP chimera depicted in the Figure was fused to the LipoF signal sequence, represented by positions 1-26 of FIG. 8.

An "isolated" nucleic acid molecule is a nucleic acid molecule separate and discrete from the whole organism with which the molecule is found in nature; or a nucleic acid molecule devoid, in whole or part, of sequences normally associated with it in nature; or a sequence, as it exists in nature, but having heterologous sequences (as defined below) in association therewith.

"Recombinant" polypeptides refer to polypeptides produced by recombinant DNA techniques; i.e., produced from cells transformed by an exogenous DNA construct encoding the desired polypeptide. "Synthetic" polypeptides are those prepared by chemical synthesis.

A "vector" is a replicon, such as a plasmid, phage, or cosmid, to which another DNA segment may be attached so as to bring about the replication of the attached segment.

A DNA "coding sequence" or a "nucleotide sequence encoding" a particular protein, is a DNA sequence which is transcribed and translated into a polypeptide in vitro or in vivo when placed under the control of appropriate regulatory elements. The boundaries of the coding sequence are determined by a start codon at the 5' (amino) terminus and a translation stop codon at the 3' (carboxy) terminus. A coding sequence can include, but is not limited to, procaryotic sequences, cDNA from eucaryotic mRNA, genomic DNA sequences from eucaryotic (e.g., mammalian) DNA, and even synthetic DNA sequences. A transcription termination sequence will usually be located 3' to the coding sequence.

DNA "control elements" refers collectively to promoters, ribosome binding sites, polyadenylation signals, transcription termination sequences, upstream regulatory domains, enhancers, and the like, which collectively provide for the transcription and translation of a coding sequence in a host cell. Not all of these control sequences need always be present in a recombinant vector so long as the desired gene is capable of being transcribed and translated.

"Operably linked" refers to an arrangement of elements wherein the components so described are configured so as to perform their usual function. Thus, control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter and the coding sequence and the promoter can still be considered "operably linked" to the coding sequence.

Similarly, a coding sequence is "operably linked to" another coding sequence (i.e., in the case of a chimeric protein) when RNA polymerase will transcribe the two coding sequences into mRNA, which is then translated into the polypeptides encoded by the two coding sequences. The coding sequences need not be contiguous to one another so long as the transcribed sequence is ultimately processed to produce the desired protein.

A control element, such as a promoter, "directs the transcription" of a coding sequence in a cell when RNA polymerase will bind the promoter and transcribe the coding sequence into mRNA, which is then translated into the polypeptide encoded by the coding sequence.

A "host cell" is a cell which has been transformed, or is capable of transformation, by an exogenous nucleic acid molecule.

A cell has been "transformed" by exogenous DNA when such exogenous DNA has been introduced inside the cell membrane. Exogenous DNA may or may not be integrated (covalently linked) into chromosomal DNA making up the genome of the cell. In procaryotes and yeasts, for example, the exogenous DNA may be maintained on an episomal element, such as a plasmid. With respect to eucaryotic cells, a stably transformed cell is one in which the exogenous DNA has become integrated into the chromosome so that it is inherited by daughter cells through chromosome replication. This stability is demonstrated by the ability of the eucaryotic cell to establish cell lines or clones comprised of a population of daughter cells containing the exogenous DNA.

"Homology" refers to the percent similarity between two polynucleotide or two polypeptide moieties. Two DNA, or two polypeptide sequences are "substantially homologous" to each other when the sequences exhibit at least about 80%-85%, preferably at least about 90%, and most preferably at least about 95%-98% sequence similarity or identity over a defined length of the molecules. As used herein, substantially homologous also refers to sequences showing complete identity to the specified DNA or polypeptide sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in *Atlas of Protein Sequence and Structure* M. O. Dayhoff ed., 5 Suppl. 3:353-358, National biomedical Research Foundation, Washington, D.C., which adapts the local homology algorithm of Smith and Waterman (1981) *Advances in Appl. Math.* 2:482-489 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art.

See, e.g., Sambrook et al., supra; DNA Cloning, supra; Nucleic Acid Hybridization, supra.

The term "functionally equivalent" intends that the amino acid sequence of the CAMP factor is one that will elicit a substantially equivalent or enhanced immunological response, as defined above, as compared to the response elicited by a CAMP factor having identity with either the mature sequence for the reference CAMP factor, or an immunogenic portion thereof.

A "heterologous" region of a DNA construct is an identifiable segment of DNA within or attached to another DNA molecule that is not found in association with the other molecule in nature. Thus, when the heterologous region encodes a bacterial gene, the gene will usually be flanked by DNA that does not flank the bacterial gene in the genome of the source bacteria. Another example of the heterologous coding sequence is a construct where the coding sequence itself is not found in nature (e.g., synthetic sequences having codons different from the native gene). Allelic variation or naturally occurring mutational events do not give rise to a heterologous region of DNA, as used herein.

As used herein, a "biological sample" refers to a sample of tissue or fluid isolated from a subject, including but not limited to, for example, blood, plasma, serum, fecal matter, urine, bone marrow, bile, spinal fluid, lymph fluid, samples of the skin, external secretions of the skin, respiratory, intestinal, and genitourinary tracts, tears, saliva, milk, blood cells, organs, biopsies and also samples of in vitro cell culture constituents including but not limited to conditioned media resulting from the growth of cells and tissues in culture medium, e.g., recombinant cells, and cell components.

As used herein, the terms "label" and "detectable label" refer to a molecule capable of detection, including, but not limited to, radioactive isotopes, fluorescers, chemiluminescers, enzymes, enzyme substrates, enzyme cofactors, enzyme inhibitors, chromophores, dyes, metal ions, metal sols, ligands (e.g., biotin or haptens) and the like. The term "fluorescer" refers to a substance or a portion thereof which is capable of exhibiting fluorescence in the detectable range. Particular examples of labels which may be used under the invention include fluorescein, rhodamine, dansyl, umbelliferone, Texas red, luminol, NADPH and α-β-galactosidase.

The term "treatment" as used herein refers to either (i) the prevention of infection or reinfection (prophylaxis), or (ii) the reduction or elimination of symptoms of the disease of interest (therapy).

By "vertebrate subject" is meant any member of the subphylum cordata, including, without limitation, mammals such as cattle, sheep, pigs, goats, horses, and humans; domestic animals such as dogs and cats; and birds, including domestic, wild and game birds such as cocks and hens including chickens, turkeys and other gallinaceous birds; and fish. The term does not denote a particular age. Thus, both adult and newborn animals, as well as fetuses, are intended to be covered.

B. General Methods

Central to the present invention is the discovery that the CAMP factor is capable of eliciting a protective immune response in a vertebrate subject. The gene for the *S. uberis* CAMP factor has been isolated and characterized and the CAMP factor encoded thereby sequenced. The protein product from the *S. uberis* CAMP factor gene has been shown to protect cattle from subsequent challenge with *S. uberis*. Additionally, chimeric proteins, including CAMP factor epitopes from multiple bacterial species, confer protection against bacterial challenge and provide a vaccine antigen which is cross-reactive with various bacterial species and which is more immunogenic than the individual CAMP factors. Moreover, antibodies raised against purified *S. uberis* CAMP factor cross-react with *S. agalactiae* protein B. As shown in the examples, the *S. uberis* CAMP factor is secreted when produced recombinantly in *E. coli*.

The complete coding sequence of *S. uberis* CAMP factor is shown in FIG. 2 (SEQ ID NO: 1). The *S. uberis* CAMP factor gene encodes a preprotein of about 258 amino acids (amino acid residues 1 through 258, inclusive, of FIG. 2, SEQ ID NO:2) that includes an N-terminal signal sequence approximately 30 amino acids in length (see, FIG. 6B; SEQ ID NO:7). The precursor molecule has a calculated molecular weight of approximately 28.5 kDa. The mature *S. uberis* CAMP factor thus includes amino acid residues 31 through 258, inclusive, as depicted in FIG. 2. Additionally, the coding sequence of *S. agalactiae* CAMP factor is shown in FIG. 3 (SEQ ID NO:3). The *S. agalactiae* CAMP factor gene encodes a preprotein of about 255 amino acids (amino acid residues 1 through 255, inclusive, of FIG. 3, SEQ ID NO:4) that includes an N-terminal signal sequence approximately 29 amino acids in length (see, FIG. 6A, SEQ ID NO:6). As discussed further below, the portion of the CAMP factor gene encoding the signal sequence can be included in constructs that encode the CAMP factor and chimeras thereof to direct secretion of the CAMP factor upon expression. Alternatively, such constructs can include a heterologous signal sequence. Additionally, the CAMP factor signal sequence and the nucleic acid sequence encoding the same can be used with heterologous proteins and nucleic acid molecules, to aid in the secretion thereof.

As shown in FIG. 4, alignment of the amino acid sequence of the *S. agalactiae* CAMP factor with the deduced sequence of the *S. uberis* CAMP factor shows an overall similarity of about 69%. Approximately 63% of the amino acid residues are identical. The two proteins can be separated into low and high homology regions. The majority of conserved amino acids are located after the leucine residue corresponding to amino acid 87 of *S. agalactiae* CAMP and amino acid 90 of *S. uberis* CAMP. The low homology region (also termed the N-terminal variable region herein) thus includes residues 1-90 of *S. uberis* and 1-87 of *S. agalactiae* and displays an overall homology of about 49% between the two species. In sum, the first third of the two CAMP proteins includes nonidentical signal sequences of 29 amino acids (*S. agalactiae*) and 30 amino acids (*S. uberis*), respectively, followed by regions of 57 amino acids and 59 amino acids, respectively, which do not share extensive homology. The high homology region found from residue 91 on of *S. uberis* and 88 on of *S. agalactiae*, displays an overall homology of about 79%.

The exact localization and sequence of the CAMP factor gene allows for in vitro mutagenesis studies to assess the functions of different domains on the CAMP protein. Also, the present data permits the generation of stable CAMP factor-synthesis deficient mutants through gene replacement and other molecular techniques. Comparison of the virulence of native and mutant *S. uberis* strains in animals provides important information regarding the contribution of the CAMP factor to the pathogenicity of bacteria expressing CAMP factors.

Epitopes derived from the various CAMP factors from multiple bacterial species can be used in combination in order to provide a multivalent vaccine that confers broad protection against bacterial infection, such as mastitis. Such epitopes can be provided individually in one or more subunit vaccine compositions, or can be conveniently provided as a chimeric protein, expressed recombinantly as a fusion protein or expressed individually and subsequently fused.

In particular, as explained above, the CAMP factor is found in a variety of bacterial species, including, without limitation S. uberis, group B streptococci (GBS) such as S. agalactiae (Jürgens et al. (1985) J. Chromatogr. 348:363-370; Rühlmann et al. (1988) FEBS Lett 235:262-266; Schneewind et al. (1988) Infect. Immun. 56:2174-2179), A. pleuropneumoniae (Frey et al. (1989) Infect. Immun. 57:2050-2056), group A streptococci (GAS), such as S. pyogenes (Gase et al. (1999) Infect. Immun. 67:4725-4731), and streptococci from serogroups C, M, P, R, and U, Listeria monocytogenes and Listeria seeligeri (Rocourt, J. and Grimont, P. A. D. (1983) Int. J. Syst. Bacteriol. 33:866-869), Aeromonas sp. (Figura, N. and Guglielmetti, P. (1987) J. Clin. Microbiol. 25:1341-1342), Rhodococcus equi (Fraser, G. (1961) Nature 189:246), and certain Vibrio spp. (Kohler, W. (1988) Zentralbl. Bakteriol. Mikrobiol. Hyg. Ser. A 270:35-40). With the exception of the N-terminal region, the amino acid sequences of the CAMP factor proteins produced by the various bacterial strains are highly conserved. Other localized variable regions occur throughout the CAMP factor molecule. See, for example FIG. 4. Therefore, it is desirable to construct multiple epitope CAMP factor fusion proteins comprising epitopes derived from both the highly conserved regions of the CAMP factor, and the variable regions of the CAMP factor proteins from more than one of the above bacterial species. Experiments performed in support of the present invention have demonstrated that such a protein is capable of eliciting immunity against *streptococcal* infection while providing the additional economic advantage of minimizing the number of antigens present in the final formulation, and concomitantly reducing the cost of producing the formulation.

Thus, the CAMP factor chimeras of the present invention can include, for example, multiple epitopes derived from the N-terminal variable region of the CAMP factor, such as contiguous amino acid sequences comprising at least about 5-10 up to about 50-90 amino acids, or any integer therebetween, from the N-terminal variable region of the CAMP factor represented by amino acids 1-90 of the S. uberis CAMP factor, and amino acids 1-87 of the S. agalactiae CAMP factor, from any of the various bacterial species described herein, preferably 20 or more contiguous amino acids from this region, more preferably about 30-80, and even more preferably 40-60 contiguous amino acids from this region. Preferably, the chimeras will include epitopes from the N-terminal variable region from more than one *streptococcal* CAMP factor, such as from S. uberis and S. agalactiae. The chimeras optionally include additional epitopes from other regions of the CAMP factor and may include the remainder of the CAMP factor molecule from at least one bacterial species, and optionally more than one bacterial species. Additionally, multiple epitopes from the same species can be present.

Epitopes for use in the CAMP factor chimeras of the present invention can be readily identified by aligning the sequences of CAMP factors from, e.g., two or more of the bacterial species listed above, and searching for the variable and conserved regions. Normally, it is desirable to include epitopes from the variable regions of the CAMP factors in order to confer broad-based protection against a variety of bacteria. Additional epitopes can be identified using techniques well known in the art, such as using standard antigenicity and hydropathy plots, for example those calculated using, e.g., the Omiga version 1.0 software program available from the Oxford Molecular Group. This computer program employs the Hopp/Woods method, Hopp et al., *Proc. Natl. Acad. Sci USA* (1981) 78:3824-3828 for determining antigenicity profiles, and the Kyte-Doolittle technique, Kyte et al., *J. Mol. Biol.* (1982) 157:105-132 for hydropathy plots. This program can be used with the following parameters: averaging results over a window of 7; determining surface probability according to Emini; chain flexibility according to Karplus-Schulz; antigenicity index according to Jameson-Wolf; secondary structure according to Garnier-Osguthorpe-Robson; secondary structure according to Chou-Fasman; and identifying predicted glycosylation sites. One of skill in the art can readily use the information obtained in combination with teachings of the present specification to identify antigenic regions which may be employed in constructing the chimeric proteins of the invention.

Generally, the various epitopes will be separated by spacer sequences. The spacer sequence is typically an amino acid sequence of from 1-500 amino acids, preferably 1-100 amino acids, more preferably 1-50 amino acids, preferably 1-25 amino acids, and most preferably 1-10 amino acids, or any integer between 1-500. The spacer amino acids may be the same or different between the various epitopes. Particularly preferred amino acids for use as spacers are amino acids with small side groups, such as alanine, glycine and valine.

The chimeras of the present invention may also include a signal sequence. The signal sequence can be a CAMP factor signal sequence, such as either of the signal sequences depicted in FIGS. 6A and 6B, or can be any of various heterologous sequences. Non-limiting examples of particularly suitable signal sequences include the E. coli LipoF signal sequence, and the OmpF signal sequence. The LipoF signal sequence aids in efficient secretion from the bacterial host cell and becomes bound to the host cell membrane via the lipid-moiety. The protein may then be extracted from the cell surface via differential solubilization with a detergent such as Sarkosyl or TritonX-100 (see the examples). Additional signal sequences for use herein are discussed further below.

An especially preferred embodiment of the present invention is a chimera which includes one or more epitopes from any of the various CAMP factors described herein, interposed within a full-length CAMP factor backbone from a different bacterium than a bacterium from which at least one of the epitopes is obtained, if multiple epitopes are used. The backbone may or may not include the signal sequence from the CAMP factor in question. Preferably, the epitope is from the N-terminal variable region of the CAMP factor represented by residues 1-90 of S. uberis and 1-87 of S. agalactiae, respectively. It is to be understood that this epitope can be derived from other *streptoccoal* and bacterial species that produce the CAMP factor with corresponding N-terminal variable regions. Moreover, by "interposed" is meant that the epitope is inserted somewhere internal to the full-length sequence and the term does not exclude the presence of spacer sequences between the epitope and the—and C-terminal regions of the full-length CAMP factor between which the epitope is inserted.

Such a construct is represented by the chimera shown at positions 27-314 of FIG. 8, termed "CAMP-3" herein. Amino acids 1-26 of FIG. 8 represent the E. coli LipoF signal sequence. Amino acids 27-86 in FIG. 8 correspond to amino acids 31-90 of the S. uberis CAMP factor sequence shown in FIG. 2 (amino acids 1-60, numbered relative to the mature S. uberis sequence). Amino acid 87 is a linker amino acid. Amino acids 88-144 of FIG. 8 correspond to amino acids 31-87 of the S. agalactiae sequence shown in FIG. 3 (amino acids 2-58, numbered relative to the mature S. agalactiae sequence. Amino acids 145 and 146 of FIG. 8 are spacer amino acids. Amino acids 147-314 shown in FIG. 8 correspond to amino acids 91-258 of the S. uberis CAMP factor sequence shown in FIG. 2 (amino acids 63-230, numbered relative to the mature *S. uberis* sequence). Thus, the chimera shown in FIG. 8 includes a full-length *S. uberis* backbone with an epitope from the N-terminal sequence of the CAMP factor from *S. agalactiae* inserted therein.

The CAMP factors, immunogenic fragments thereof or chimeric proteins including the same, as described above, can be provided in subunit vaccine compositions. In addition to use in vaccine compositions, the proteins or antibodies thereto can be used as diagnostic reagents to detect the presence of infection in a vertebrate subject. Similarly, the genes encoding the proteins can be cloned and used to design probes to detect and isolate homologous genes in other bacterial strains.

The vaccine compositions of the present invention can be used to treat or prevent a wide variety of bacterial infections in vertebrate subjects. For example, vaccine compositions including CAMP factors from *S. uberis*, group B streptococci (GBS), such as *S. agalactiae* and/or group A streptococci (GAS), e.g., *S. pyogenes*, and streptococci from serogroups C, M, P, R, and U, can be used to treat *streptococcal* infections in vertebrate subjects that are caused by these species. For example, *S. uberis* and *S. agalactiae* are common bacterial pathogens associated with mastitis in bovine, equine, ovine and goat species. Additionally, group B streptococci, such as *S. agalactiae*, are known to cause numerous other infections in vertebrates, including septicemia, meningitis, bacteremia, impetigo, arthritis, urinary tract infections, abscesses, spontaneous abortion etc. Hence, vaccine compositions containing *streptococcal* CAMP factors will find use in treating and/or preventing a wide variety of *streptococcal* infections.

Similarly, CAMP factors derived from *Listeria monocytogenes* and *L. seeligeri, Aeromonas* sp., *Rhodococcus equi*, and *Vibrio* spp. will find use for treating bacterial infections caused by these species. For example, CAMP factors can be used to prevent or treat listeriosis in a wide range of animals and birds, including humans. The infection can manifest itself as encephalitis and meningoencephalitis in ruminants and avian species such as geese, chickens, turkeys, ducks, canaries and parrots; septicemia in monogastric animals, neonatal ruminants and poultry; and spontaneous abortion and latent infections in a wide variety of animals. *Aeromonas* causes infections in fish, including in salmonids, aquarium fish, goldfish, freshwater and marine fish; as well as infections in caged birds and in amphibians and reptiles. *Rhodococcus equi* causes respiratory infections, lymphangitis, peritonitis, enteritis, abscesses and spontaneous abortion in horses. *Vibrio* causes vibriosis in many cultured, aquarium and wild marine and estuarine fish; infections of open wounds in cetaceans; and avian vibrionic hepatitis and avian infectious hepatitis in chickens.

Thus, it is readily apparent that CAMP factor vaccines can be used to treat and/or prevent a wide variety of bacterial infections in numerous species.

CAMP factors from various species can be used either alone or in combination in the vaccine compositions of the present invention. For example, as explained above, it will sometimes be preferable to have more than one epitope of one or more of the CAMP factors in the vaccine compositions of the present invention so that the subject in question can be provided with a broad spectrum of protection against infection. In its simplest form, this can be achieved by employing a polypeptide encoding the complete sequence of one of the CAMP factors, or by employing a combination of polypeptides encoding the sequences of two or more of the CAMP factors or epitopes of the CAMP factors. Thus, the vaccine compositions could comprise, for example various combinations of one or more of the CAMP factors, or a combination of several of the CAMP factors, or even several epitopes derived from the CAMP factors, such as in CAMP factor chimeras described above.

Furthermore, the vaccine compositions of the present invention can include other bacterial, fungal, viral or protozoal antigens. These antigens can be provided separately of even as fusion proteins comprising fragments of one or more of the CAMP factors fused to these antigens.

Production of the CAMP Factors

The above described CAMP factors and active fragments, analogs and chimeric proteins derived from the same, can be produced by a variety of methods. Specifically, the CAMP factors can be isolated directly from bacteria which express the same. This is generally accomplished by first preparing a crude extract which lacks cellular components and several extraneous proteins. The desired proteins can then be further purified i.e. by column chromatography, HPLC, immunoadsorbent techniques or other conventional methods well known in the art.

More particularly, techniques for isolating CAMP factors have been described in e.g., Skalka, B. and Smola, J. (1981) *Zbl. Bakt. Hyg., I. Abt. Orig.* A249:190-194; Skalka et al. (1980) *Zbl. Vet. Med. B*27:559-566; Skalka et al. (1979) *Zbl. Vet. Med. B*26:679-687; Bernheimer et al. (1979) *Infect. Immun.* 23:838-844; Jürgens et al. (1985) *J. Chrom.* 348:363-370; Jürgens et al. (1987) *J. Exp. Med.* 165:720-732.

Alternatively, the proteins can be recombinantly produced as described herein. As explained above, these recombinant products can take the form of partial protein sequences, full-length sequences, precursor forms that include signal sequences, mature forms without signals, or even fusion proteins (e.g., with an appropriate leader for the recombinant host, or with another subunit antigen sequence for *Streptococcus* or another pathogen).

The CAMP factor genes of the present invention can be isolated based on the ability of the protein products to display CAMP activity, using CAMP assays as described below. Thus, gene libraries can be constructed and the resulting clones used to transform an appropriate host cell. Colonies can be pooled and screened for clones having CAMP activity. Colonies can also be screened using polyclonal serum or monoclonal antibodies to the desired antigen.

Alternatively, once the amino acid sequences are determined, oligonucleotide probes which contain the codons for a portion of the determined amino acid sequences can be prepared and used to screen DNA libraries for genes encoding the subject proteins. The basic strategies for preparing oligonucleotide probes and DNA libraries, as well as their screening by nucleic acid hybridization, are well known to those of ordinary skill in the art. See, e.g., *DNA Cloning*: Vol. 1, supra; Nucleic Acid Hybridization, supra; Oligonucleotide Synthesis, supra; Sambrook et al., supra. Once a clone from the screened library has been identified by positive hybridization, it can be confirmed by restriction enzyme analysis and DNA sequencing that the particular library insert contains the desired CAMP factor gene or a homolog thereof.

Alternatively, DNA sequences encoding the proteins of interest can be prepared synthetically rather than cloned. The DNA sequences can be designed with the appropriate codons for the particular amino acid sequence. In general, one will select preferred codons for the intended host if the sequence will be used for expression. The complete sequence is assembled from overlapping oligonucleotides prepared by standard methods and assembled into a complete coding sequence. See, e.g., Edge (1981) *Nature* 292:756; Nambair et al. (1984) *Science* 223:1299; Jay et al. (1984) *J. Biol. Chem.* 259:6311.

Once coding sequences for the desired proteins have been prepared or isolated, they can be cloned into any suitable vector or replicon. Numerous cloning vectors are known to those of skill in the art, and the selection of an appropriate cloning vector is a matter of choice. Examples of recombinant DNA vectors for cloning and host cells which they can transform include the bacteriophage λ (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (*Bacillus*), pIJ61 (*Streptomyces*), pUC6 (*Streptomyces*), YIp5 (*Saccharomyces*), YCp19 (*Saccharomyces*) and bovine papilloma virus (mammalian cells). See, generally, DNA Cloning: Vols. I & II, supra; Sambrook et al., supra; B. Perbal, supra.

The gene can be placed under the control of a promoter, ribosome binding site (for bacterial expression) and, optionally, an operator (collectively referred to herein as "control" elements), so that the DNA sequence encoding the desired protein is transcribed into RNA in the host cell transformed by a vector containing this expression construction. The coding sequence may or may not contain a signal peptide or leader sequence. If signal sequences are included, they can either be the native, homologous sequences, or heterologous sequences. For example, the signal sequences for the *S. uberis* or *S. agalactiae* CAMP factors (shown in FIGS. 6A and 6B, respectively), can be used for secretion of various CAMP factors, as can a number of other signal sequences, well known in the art. Leader sequences can be removed by the host in post-translational processing. See, e.g., U.S. Pat. Nos. 4,431,739; 4,425,437; 4,338,397.

Other regulatory sequences may also be desirable which allow for regulation of expression of the protein sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

The control sequences and other regulatory sequences may be ligated to the coding sequence prior to insertion into a vector, such as the cloning vectors described above. Alternatively, the coding sequence can be cloned directly into an expression vector which already contains the control sequences and an appropriate restriction site.

In some cases it may be necessary to modify the coding sequence so that it may be attached to the control sequences with the appropriate orientation; i.e., to maintain the proper reading frame. It may also be desirable to produce mutants or analogs of the CAMP factor of interest. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are described in, e.g., Sambrook et al., supra; *DNA Cloning*, Vols. I and II, supra; *Nucleic Acid Hybridization*, supra.

The expression vector is then used to transform an appropriate host cell. A number of mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human hepatocellular carcinoma cells (e.g., Hep G2), Madin-Darby bovine kidney ("MDBK") cells, as well as others. Similarly, bacterial hosts such as *E. coli, Bacillus subtilis*, and *Streptococcus* spp., will find use with the present expression constructs. Yeast hosts useful in the present invention include inter alia, *Saccharomyces cerevisiae, Candida albicans, Candida maltosa, Hansenula polymorpha, Kluyveromyces fragilis, Kluyveromyces lactis, Pichia guilermondii, Pichia pastoris, Schizosaccharomyces pombe* and *Yarrowia lipolytica*. Insect cells for use with baculovirus expression vectors include, inter alia, *Aedes aegypti, Autographa californica, Bombyx mori, Drosophila melanogaster, Spodoptera fruperda*, and *Trichoplusia ni*.

Depending on the expression system and host selected, the proteins of the present invention are produced by culturing host cells transformed by an expression vector described above under conditions whereby the protein of interest is expressed. The protein is then isolated from the host cells and purified. If the expression system secretes the protein into the growth media, the protein can be purified directly from the media. If the protein is not secreted, it is isolated from cell lysates. The selection of the appropriate growth conditions and recovery methods are within the skill of the art.

The proteins of the present invention may also be produced by chemical synthesis such as solid phase peptide synthesis, using known amino acid sequences or amino acid sequences derived from the DNA sequence of the genes of interest. Such methods are known to those skilled in the art. Chemical synthesis of peptides may be preferable if a small fragment of the antigen in question is capable of raising an immunological response in the subject of interest.

The CAMP factors, fragments, analogs and chimeras containing the same, can be tested for CAMP activity using any of several standard tests. For example, CAMP factors are known to display lytic action on a variety of target cells including bovine and ovine erythrocytes. Thus, a convenient method for testing for CAMP factor activity utilizes standard hemolytic reactions using ovine or bovine erythrocytes. See, e.g., Christie et al. (1944) *Aus. J. Exp. Biol. Med. Sci.* 22:197-200; Brown et al. (1974) *Infect. Immun.* 9:377-383; Darling, C. L. (1975) *J. Clin. Microbiol.* 1:171; Wilkinsin, H. W. (1977) *J. Clin. Microbiol.* 6:42; Bernheimer et al. (1979) *Infect. Immun.* 23:838-844; Skalka, B. and Smola, J. (1981) *Zbl. Bakt. Hyg., I. Abt. Orig.* A249:190-194; Huser et al. (1983) *J. Gen. Microbiol.* 129:1295.

Activity can also be tested by monitoring the release of entrapped marker molecules from liposomes made from materials susceptible to disruption by CAMP factors. For example, CAMP activity can be monitored using [$^{14}$C]glucose-containing liposomes prepared from, e.g., sphingomyelin, cholesterol and dicetyl phosphate, and measuring the release of trapped [$^{14}$C]glucose due to disruption of the liposomes by the CAMP factor. See, e.g., Bernheimer et al. (1979) *Infect. Immun.* 23:838-844. Similarly, ATP release from liposomes in the presence of CAMP factor can be monitored as described in Sterzik et al. (1984) "Interaction of the CAMP factor from *S. agalactiae* with artificial membranes" In: Alouf et al., eds. *Bacterial protein toxins*, London: Academic Press Inc., 1984:195-196; and Sterzik et al. (1985) *Zentralbl. Bakteriol. Mikrobiol. Hyg. Abt.* 1 Suppl. 15:101-108. See, also Fehrenbach et al. (1984) "Interaction of amphiphilic bacterial polypeptides with artificial membranes." In: Alouf et al., eds. *Bacterial protein toxins*, London: Academic Press Inc., 1984:317-324.

The CAMP factors of the present invention or their fragments can be used to produce antibodies, both polyclonal and monoclonal. If polyclonal antibodies are desired, a selected mammal, (e.g., mouse, rabbit, goat, horse, etc.) is immunized with an antigen of the present invention, or its fragment, or a mutated antigen. Serum from the immunized animal is collected and treated according to known procedures. See, e.g., Jurgens et al. (1985) *J. Chrom.* 348:363-370. If serum containing polyclonal antibodies is used, the polyclonal antibodies can be purified by immunoaffinity chromatography, using known procedures.

Monoclonal antibodies to the CAMP factors and to the fragments thereof, can also be readily produced by one skilled in the art. The general methodology for making monoclonal antibodies by using hybridoma technology is well known. Immortal antibody-producing cell lines can be created by cell fusion, and also by other techniques such as direct transformation of B lymphocytes with oncogenic DNA, or transfection with Epstein-Barr virus. See, e.g., M. Schreier et al., *Hybridoma Techniques* (1980); Hammerling et al., *Monoclonal Antibodies and T-cell Hybridomas* (1981); Kennett et al., *Monoclonal Antibodies* (1980); see also U.S. Pat. Nos. 4,341,761; 4,399,121; 4,427,783; 4,444,887; 4,452,570; 4,466,917; 4,472,500, 4,491,632; and 4,493,890. Panels of monoclonal antibodies produced against the CAMP factor of interest, or fragment thereof, can be screened for various properties; i.e., for isotype, epitope, affinity, etc. Monoclonal antibodies are useful in purification, using immunoaffinity techniques, of the individual antigens which they are directed against. Both polyclonal and monoclonal antibodies can also be used for passive immunization or can be combined with subunit vaccine preparations to enhance the immune response.

Vaccine Formulations and Administration

The CAMP factors of the present invention can be formulated into vaccine compositions, either alone or in combination with other antigens, for use in immunizing subjects as described below. Methods of preparing such formulations are described in, e.g., *Remington's Pharmaceutical Sciences*, Mack Publishing Company, Easton, Pa., 18 Edition, 1990. Typically, the vaccines of the present invention are prepared as injectables, either as liquid solutions or suspensions. Solid forms suitable for solution in or suspension in liquid vehicles prior to injection may also be prepared. The preparation may also be emulsified or the active ingredient encapsulated in liposome vehicles. The active immunogenic ingredient is generally mixed with a compatible pharmaceutical vehicle, such as, for example, water, saline, dextrose, glycerol, ethanol, or the like, and combinations thereof. In addition, if desired, the vehicle may contain minor amounts of auxiliary substances such as wetting or emulsifying agents and pH buffering agents.

Adjuvants which enhance the effectiveness of the vaccine may also be added to the formulation. Adjuvants may include for example, muramyl dipeptides, pyridine, aluminum hydroxide, dimethyldioctadecyl ammonium bromide (DDA), oils, oil-in-water emulsions, saponins, cytokines, and other substances known in the art.

The CAMP factor may be linked to a carrier in order to increase the immunogenicity thereof. Suitable carriers include large, slowly metabolized macromolecules such as proteins, including serum albumins, keyhole limpet hemocyanin, immunoglobulin molecules, thyroglobulin, ovalbumin, and other proteins well known to those skilled in the art; polysaccharides, such as sepharose, agarose, cellulose, cellulose beads and the like; polymeric amino acids such as polyglutamic acid, polylysine, and the like; amino acid copolymers; and in-active virus particles.

The CAMP factors may be used in their native form or their functional group content may be modified by, for example, succinylation of lysine residues or reaction with Cys-thiolactone. A sulfhydryl group may also be incorporated into the carrier (or antigen) by, for example, reaction of amino functions with 2-iminothiolane or the N-hydroxysuccinimide ester of 3-(4-dithiopyridyl) propionate. Suitable carriers may also be modified to incorporate spacer arms (such as hexamethylene diamine or other bifunctional molecules of similar size) for attachment of peptides.

Other suitable carriers for the CAMP factors of the present invention include VP6 polypeptides of rotaviruses, or functional fragments thereof, as disclosed in U.S. Pat. No. 5,071,651, incorporated herein by reference. Also useful is a fusion product of a viral protein and the subject immunogens made by methods disclosed in U.S. Pat. No. 4,722,840. Still other suitable carriers include cells, such as lymphocytes, since presentation in this form mimics the natural mode of presentation in the subject, which gives rise to the immunized state. Alternatively, the proteins of the present invention may be coupled to erythrocytes, preferably the subject's own erythrocytes. Methods of coupling peptides to proteins or cells are known to those of skill in the art.

Furthermore, the CAMP factors (or complexes thereof) may be formulated into vaccine compositions in either neutral or salt forms. Pharmaceutically acceptable salts include the acid addition salts (formed with the free amino groups of the active polypeptides) and which are formed with inorganic acids such as, for example, hydrochloric or phosphoric acids, or such organic acids as acetic, oxalic, tartaric, mandelic, and the like. Salts formed from free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Injectable vaccine formulations will contain a "therapeutically effective amount" of the active ingredient, that is, an amount capable of eliciting an immune response in a subject to which the composition is administered. In the treatment and prevention of mastitis, for example, a "therapeutically effective amount" would preferably be an amount which controls infection, as measured by, e.g. the ability of the composition to retain or bring the somatic cell count in milk below about 500,000 cells per ml. The exact amount is readily determined by one skilled in the art using standard tests. The CAMP factor will typically range from about 1% to about 95% (w/w) of the composition, or even higher or lower if appropriate. With the present vaccine formulations, 20 to 500 µg of active ingredient per ml of injected solution should be adequate to raise an immunological response when a dose of 1 to 3 ml per animal is administered.

To immunize a subject, the vaccine is generally administered parenterally, usually by intramuscular injection. Other modes of administration, however, such as subcutaneous, intraperitoneal and intravenous injection, are also acceptable. The quantity to be administered depends on the animal to be treated, the capacity of the animal's immune system to synthesize antibodies, and the degree of protection desired. Effective dosages can be readily established by one of ordinary skill in the art through routine trials establishing dose response curves. The subject is immunized by administration of the vaccine in at least one dose, and preferably two doses. Moreover, the animal may be administered as many doses as is required to maintain a state of immunity to infection.

Additional vaccine formulations which are suitable for other modes of administration include suppositories and, in some cases, aerosol, intranasal, oral formulations, and sustained release formulations. For suppositories, the vehicle composition will include traditional binders and carriers, such as, polyalkaline glycols, or triglycerides. Such suppositories may be formed from mixtures containing the active ingredient in the range of about 0.5% to about 10% (w/w), preferably about 1% to about 2%. Oral vehicles include such normally employed excipients as, for example, pharmaceutical grades of mannitol, lactose, starch, magnesium, stearate, sodium saccharin cellulose, magnesium carbonate, and the like. These oral vaccine compositions may be taken in the form of solutions, suspensions, tablets, pills, capsules, sustained release formulations, or powders, and contain from about 10% to about 95% of the active ingredient, preferably about 25% to about 70%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

Controlled or sustained release formulations are made by incorporating the protein into carriers or vehicles such as liposomes, nonresorbable impermeable polymers such as ethylenevinyl acetate copolymers and Hytrel® copolymers, swellable polymers such as hydrogels, or resorbable polymers such as collagen and certain polyacids or polyesters such as those used to make resorbable sutures. The CAMP factors can also be delivered using implanted mini-pumps, well known in the art.

The CAMP factors of the instant invention can also be administered via a carrier virus which expresses the same. Carrier viruses which will find use with the instant invention include but are not limited to the vaccinia and other pox viruses, adenovirus, and herpes virus. By way of example, vaccinia virus recombinants expressing the novel proteins can be constructed as follows. The DNA encoding the particular protein is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the instant protein into the viral genome. The resulting TK$^-$ recombinant can be selected by culturing the cells in the presence of 5-bromodeoxyuridine and picking viral plaques resistant thereto.

An alternative route of administration involves gene therapy or nucleic acid immunization. Thus, nucleotide sequences (and accompanying regulatory elements) encoding the subject CAMP factors can be administered directly to a subject for in vivo translation thereof. Alternatively, gene transfer can be accomplished by transfecting the subject's cells or tissues ex vivo and reintroducing the transformed material into the host. DNA can be directly introduced into the host organism, i.e., by injection (see International Publication No. WO/90/11092; and Wolff et al. (1990) *Science* 247:1465-1468). Liposome-mediated gene transfer can also be accomplished using known methods. See, e.g., Hazinski et al. (1991) *Am. J. Respir. Cell Mol. Biol.* 4:206-209; Brigham et al. (1989) *Am. J. Med. Sci.* 298:278-281; Canonico et al. (1991) *Clin. Res.* 39:219A; and Nabel et al. (1990) *Science* 1990) 249:1285-128.8. Targeting agents, such as antibodies directed against surface antigens expressed on specific cell types, can be covalently conjugated to the liposomal surface so that the nucleic acid can be delivered to specific tissues and cells susceptible to infection.

Diagnostic Assays

As explained above, the CAMP factors, variants and immunogenic fragments thereof and chimeras comprising CAMP factor epitopes, may also be used as diagnostics to detect the presence of reactive antibodies of *streptococcus*, for example *S. uberis, S. agalactiae* and/or *S. dysgalactiae*, in a biological sample in order to determine the presence of *streptococcus* infection. For example, the presence of antibodies reactive with a CAMP factor can be detected using standard electrophoretic and immunodiagnostic techniques, including immunoassays such as competition, direct reaction, or sandwich type assays. Such assays include, but are not limited to, Western blots; agglutination tests; enzyme-labeled and mediated immunoassays, such as ELISAs; biotin/avidin type assays; radioimmunoassays; immunoelectrophoresis; immunoprecipitation, etc. The reactions generally include revealing labels such as fluorescent, chemiluminescent, radioactive, enzymatic labels or dye molecules, or other methods for detecting the formation of a complex between the antigen and the antibody or antibodies reacted therewith.

The aforementioned assays generally involve separation of unbound antibody in a liquid phase from a solid phase support to which antigen-antibody complexes are bound. Solid supports which can be used in the practice of the invention include substrates such as nitrocellulose (e.g., in membrane or microtiter well form); polyvinylchloride (e.g., sheets or microtiter wells); polystyrene latex (e.g., beads or microtiter plates); polyvinylidine fluoride; diazotized paper; nylon membranes; activated beads, magnetically responsive beads, and the like.

Typically, a solid support is first reacted with a solid phase component (e.g., one or more CAMP factors) under suitable binding conditions such that the component is sufficiently immobilized to the support. Sometimes, immobilization of the antigen to the support can be enhanced by first coupling the antigen to a protein with better binding properties. Suitable coupling proteins include, but are not limited to, macromolecules such as serum albumins including bovine serum albumin (BSA), keyhole limpet hemocyanin, immunoglobulin molecules, thyroglobulin, ovalbumin, and other proteins well known to those skilled in the art. Other molecules that can be used to bind the antigens to the support include polysaccharides, polylactic acids, polyglycolic acids, polymeric amino acids, amino acid copolymers, and the like. Such molecules and methods of coupling these molecules to the antigens, are well known to those of ordinary skill in the art. See, e.g., Brinkley, M. A. *Bioconjugate Chem.* (1992) 3:2-13; Hashida et al., *J. Appl. Biochem.* (1984) 6:56-63; and Anjaneyulu and Staros, *International J. of Peptide and Protein Res.* (1987) 30:117-124.

After reacting the solid support with the solid phase component, any non-immobilized solid-phase components are removed from the support by washing, and the support-bound component is then contacted with a biological sample suspected of containing ligand moieties (e.g., antibodies toward the immobilized antigens) under suitable binding conditions. After washing to remove any non-bound ligand, a secondary binder moiety is added under suitable binding conditions, wherein the secondary binder is capable of associating selectively with the bound ligand. The presence of the secondary binder can then be detected using techniques well known in the art.

More particularly, an ELISA method can be used, wherein the wells of a microtiter plate are coated with a CAMP factor protein. A biological sample containing or suspected of containing anti-CAMP factor immunoglobulin molecules is then added to the coated wells. After a period of incubation sufficient to allow antibody binding to the immobilized antigen, the plate(s) can be washed to remove unbound moieties and a detectably labeled secondary binding molecule added. The secondary binding molecule is allowed to react with any captured sample antibodies, the plate washed and the presence of the secondary binding molecule detected using methods well known in the art.

Thus, in one particular embodiment, the presence of bound anti-CAMP factor ligands from a biological sample can be readily detected using a secondary binder comprising an antibody directed against the antibody ligands. A number of anti-bovine immunoglobulin (Ig) molecules are known in the art which can be readily conjugated to a detectable enzyme label, such as horseradish peroxidase, alkaline phosphatase or urease, using methods known to those of skill in the art. An appropriate enzyme substrate is then used to generate a detectable signal. In other related embodiments, competitive-type ELISA techniques can be practiced using methods known to those skilled in the art.

Assays can also be conducted in solution, such that the CAMP factor proteins and antibodies specific for those proteins form complexes under precipitating conditions. In one particular embodiment, CAMP factor proteins can be attached to a solid phase particle (e.g., an agarose bead or the like) using coupling techniques known in the art, such as by direct chemical or indirect coupling. The antigen-coated particle is then contacted under suitable binding conditions with a biological sample suspected of containing antibodies for the CAMP factor proteins. Cross-linking between bound antibodies causes the formation of particle-antigen-antibody complex aggregates which can be precipitated and separated from the sample using washing and/or centrifugation. The reaction mixture can be analyzed to determine the presence or absence of antibody-antigen complexes using any of a number of standard methods, such as those immunodiagnostic methods described above.

In yet a further embodiment, an immunoaffinity matrix can be provided, wherein a polyclonal population of antibodies from a biological sample suspected of containing anti-CAMP factor molecules is immobilized to a substrate. In this regard, an initial affinity purification of the sample can be carried out using immobilized antigens. The resultant sample preparation will thus only contain anti-*streptococcus* moieties, avoiding potential nonspecific binding properties in the affinity support. A number of methods of immobilizing immunoglobulins (either intact or in specific fragments) at high yield and good retention of antigen binding activity are known in the art. Not being limited by any particular method, immobilized protein A or protein G can be used to immobilize immunoglobulins.

Accordingly, once the immunoglobulin molecules have been immobilized to provide an immunoaffinity matrix, labeled CAMP factor proteins are contacted with the bound antibodies under suitable binding conditions. After any non-specifically bound antigen has been washed from the immunoaffinity support, the presence of bound antigen can be determined by assaying for label using methods known in the art.

Additionally, antibodies raised to the CAMP factor proteins, rather than the CAMP factors themselves, can be used in the above-described assays in order to detect the presence of antibodies to the proteins in a given sample. These assays are performed essentially as described above and are well known to those of skill in the art.

The above-described assay reagents, including the CAMP factor proteins, or antibodies thereto, can be provided in kits, with suitable instructions and other necessary reagents, in order to conduct immunoassays as described above. The kit can also contain, depending on the particular immunoassay used, suitable labels and other packaged reagents and materials (i.e. wash buffers and the like). Standard immunoassays, such as those described above, can be conducted using these kits.

Below are examples of specific embodiments for carrying out the present invention. The examples are offered for illustrative purposes only, and are not intended to limit the scope of the present invention in any way.

Deposits of Strains Useful in Practicing the Invention

A deposit of biologically pure cultures of the following strains was made with the American Type Culture Collection, 10801 University Boulevard, Manassas, Va., under the provisions of the Budapest Treaty. The accession number indicated was assigned after successful viability testing, and the requisite fees were paid. The designated deposits will be maintained for a period of thirty (30) years from the date of deposit, or for five (5) years after the last request for the deposit, whichever is longer. Should a culture become non-viable or be inadvertently destroyed, or, in the case of plasmid-containing strains, lose its plasmid, it will be replaced with a viable culture(s) of the same taxonomic description.

Should there be a discrepancy between the sequence presented in the present application and the sequence of the gene of interest in the deposited plasmid due to routine sequencing errors, the sequence in the deposited plasmid controls.

| Strain | Deposit Date | ATCC No. |
| --- | --- | --- |
| pJLD21 in *E. coli* JF1754 | Jun. 9, 1995 | 69837 |

C. Experimental

Materials and Methods

Enzymes were purchased from commercial sources, and used according to the manufacturers' directions. Radionucleotides and nitrocellulose filters were also purchased from commercial sources.

In the isolation of DNA fragments, except where noted, all DNA manipulations were done according to standard procedures. See, Sambrook et al., supra. Restriction enzymes, $T_4$ DNA ligase, *E. coli*, DNA polymerase I, Klenow fragment, and other biological reagents can be purchased from commercial suppliers and used according to the manufacturers' directions. Double stranded DNA fragments were separated on agarose gels.

Bacterial Strains, Plasmids and Growth Conditions:

Except where indicated, the *E. coli* strain used for cloning the *S. uberis* CAMP factor gene was JF1754 (hsdR lac gal metB leuB hisB) (McNeil, J. B. and Friesen, J. D. (1981) *Mol. Gen. Genet.* 184:386-393). Competent *E. coli* JF1754 was made as previously described (Hanahan, D. "Techniques for transformation of *E. coli*." In: Glover DM, ed. DNA cloning (Volume I): a practical approach. Oxford: IRL Press, 1985: 109-135). *E. coli* strains used for production of the chimeric CAMP factor were XLI Blue MRF (recA 1, endA1, gyrA96, thi-1, hsdR17, supE44, relA1, lac[F'proAB lacI$^q$ZΔM15 Tn10(TetR] (Stratagene, La Jolla, Calif.); and J5, ATCC Accession No. 43745, *J. Clin. Microbiol* (1987) 25:1009-1013.

*E. coli* cells were grown in Luria broth (Difco Laboratories) or on Luria-agar (Difco Laboratories) plates. Ampicillin was used at 50 µg/ml for the growth of *E. coli* strains containing recombinant plasmids. Four *S. uberis* strains, as well as *S. agalactiae* and *S. aureus*, were obtained from the American Type Culture Collection (ATCC Accession Nos. 9927, 13386, 13387, 19436, 27541 and 25923, respectively). Other *S. uberis* strains are field isolates kindly provided by M. Chirino-Trejo, University of Saskatchewan. All *streptococcal* strains were grown in brain heart infusion broth (BHI, Difco Laboratories) or on base #2 blood agar plates with 5% sheep blood (PML microbiologicals).

The cloning vector pTZ18R (Mead et al. (1986) *Protein Eng.* 1:67-74) was obtained from Pharmacia Canada Ltd. The cloning vectors used for preparing the chimeric CAMP constructs were pAA556a and pET15-b.

Preparation of *S. aureus* Beta-Toxin:

*S. aureus* was cultured in BHI for 18 h at 37° C. and the supernatant obtained after centrifugation at 5,000 g was sterilized by filtration through a 0.22-µM filter (Nalge company). This material, referred to as crude beta-toxin, was stored at −20° C.

CAMP Reaction

Bacteria were screened for CAMP activity as described (Schneewind et al. (1988) *Infect. Immun.* 56:2174-2179). Briefly, strains were streaked perpendicular to a streak of beta-toxin-producing *S. aureus* on blood agar plates and after 6 h-20 h incubation at 37° C., they were observed for hemolysis.

Purification of CAMP Factor

CAMP factor was partially purified from the culture supernatant of *S. uberis* (ATCC Accession No. 9927) by Octyl-Sepharose CL-4B (Pharmacia) chromatography as described by Jürgens et al. (1985) *J. Chrom.* 348:363-370.

Polyclonal Antibodies

To analyze the recombinant CAMP factor of *S. uberis*, polyclonal antibodies directed against the purified CAMP factor were obtained. Mice were immunized by intraperitoneal injection of 20 µg of the purified CAMP protein with complete Freund's adjuvant. This primary immunization was followed 3 weeks later by the second intraperitoneal injection of the same amount of CAMP protein with incomplete Freund adjuvant and another 3 weeks later by the third intravenous injection of 20 µg of CAMP protein with incomplete Freund adjuvant. The blood serum samples were then taken 10 days later.

PAGE and Immunoblotting

Protein samples of *S. agalactiae* and *E. coli* were obtained from culture supernatants by trichloroacetic acid (TCA)-precipitation at a final concentration of 10%. SDS-polyacrylamide gel electrophoresis (PAGE) of proteins was performed as described by Laemmli (Laemmli, U. K. (1970) *Nature* 227:680-685). Proteins were electroblotted onto nitrocellulose membranes as recommended by the supplier (Bio-Rad) and the blots were developed as described elsewhere (Theisen, M. and Potter, A. A. (1992) *J. Bacteriol.* 174:17-23) with the following differences. The first antiserum used was mouse polyclonal antiserum against partially-purified *S. uberis* CAMP protein, and it was absorbed with antigens of the *E. coli* host strain as described previously (Frey et al. (1989) *Infect. Immun.* 57:2050-2056). The second antibody used in blotting procedure was the goat anti-mouse IgG coupled to alkaline phosphatase (Kirkegaard & Perry Laboratories, Inc.).

DNA Manipulations

All molecular techniques were as recommended by the supplier (Pharmacia Canada Ltd.) or Sambrook et al., supra. Chromosomal DNA of *S. uberis* was prepared from cells grown in 100 ml BHI plus 5% (w/v) glycine. Cells were pelleted and resuspended in 2.5 ml of TES buffer (30 mM Tris-HCl, 5 mM EDTA, 50 mM NaCl; pH 8.0) with 25% sucrose and 1.6 mg/ml lysozyme (Sigma). The suspension was incubated for 1 h at 37° C., followed by freezing at −70° C. The frozen cells were thawed in a 65° C. water bath. EDTA and proteinase K (Pharmacia) were added to final concentrations of 20 mM and 1.2 mg/ml, respectively, before incubation at 65° C. for 30 min. To lyse cells completely, sarkosyl was added to 1% and incubated at 37° C. for 1 h. Two ml of TE buffer (10 mM Tris-HCl, 1 mM EDTA; pH 8.9) was added prior to phenol: chloroform extraction. DNA was recovered by ethanol precipitation and was treated with RNase (Pharmacia Canada Ltd.).

Size-fractionated Sau3AI-digested chromosomal DNA fragments were isolated by sucrose density gradient centrifugation (Sambrook et al., supra).

DNA sequence was determined by the dideoxy-chain termination method of Sanger et al. (1977) *Proc. Natl. Acad. Sci. USA* 74:5463-5467 on double-stranded plasmid templates by using a $T7$ Sequencing kit (Pharmacia Canada Ltd.).

RNA Analyses

RNA from *E. coli* strains was isolated as described previously (Lloubes et al. (1986) *Nucleic Acid Res.* 14:2621-2636) with an additional RNase-free DNase I digestion. RNA from *S. uberis* was prepared as follows. The cell pellet from a 10 ml culture ($OD_{600}$=0.6) was resuspended in 250 µl of TE buffer (pH 8.0) containing 500 u of mutanolysin (Sigma) and incubated at 37° C. for 30 min. Lysis buffer (250 µl)(60 mM Tris-HCl pH 7.4, 200 mM NaCl, 10 mM EDTA, 2% SDS) and 100 µg/ml (final concentration) of proteinase K was added and the incubation continued for 1 h. The sample was extracted once with 65° C. phenol (water saturated, pH 4.0) and twice with room temperature phenol. RNA was recovered by ethanol precipitation and treated with DNase I (Pharmacia Canada Ltd.).

Primer extension assay was performed as described by Miller et al. (1986) *Nucleic Acids Res.* 14:7341-60. RNasin and moloney murine leukemia virus reverse transcriptase were obtained from Pharmacia Canada Ltd.

EXAMPLE 1

Cloning and Expression of the *S. Uberis* CAMP Factor Gene

Chromosomal DNA of *S. uberis* (ATCC 9927) was partially digested with Sau3AI and size fractionated in a sucrose gradient; from this, 2- to 5-kb DNA fragments were recovered. The ends of these fragments were partially filled in with dGTP and dATP and ligated into pTZ18R which was cut with SalI and partially filled in with dTTP and dCTP. Following transformation of *E. coli* JF1754 competent cells, clones expressing the CAMP factor gene were identified on blood plates with ampicillin and beta-toxin on the surface. Six clones from a total of 10,000 were phenotypically hemolytic and each one mediated a distinct CAMP reaction. One of them, containing recombinant plasmid pJLD21, was selected for further study.

Plasmid pJLD21 contained a 5.2 kb insert fragment and the CAMP factor gene, cfu, was localized within a 3.2 kb BamHI fragment after the CAMP-positive subclone pJLD21-2 was generated (FIG. 1). This subclone was further analyzed with more restriction enzymes for sequencing purposes.

To study the expression of the recombinant CAMP factor, SDS-PAGE analysis of supernatant proteins from Cfu+ E. coli JF1754(pJLD21) and host E. coli JF1754 (pTZ18R) was performed. Compared to the vector control, no distinguishable band was observed in the lane containing supernatant from the Cfu+ clone, indicating that either expression was at a very low level or the protein was not secreted efficiently. To identify the CAMP factor encoded by pJLD21, the proteins separated by SDS-PAGE were transferred to a nitrocellulose membrane and immunoblotted. The Cfu+ E. coli clone carrying pJLD21 expressed a protein with molecular weight of 28,000, similar to the native CAMP factor of S. uberis.

Figure 5:
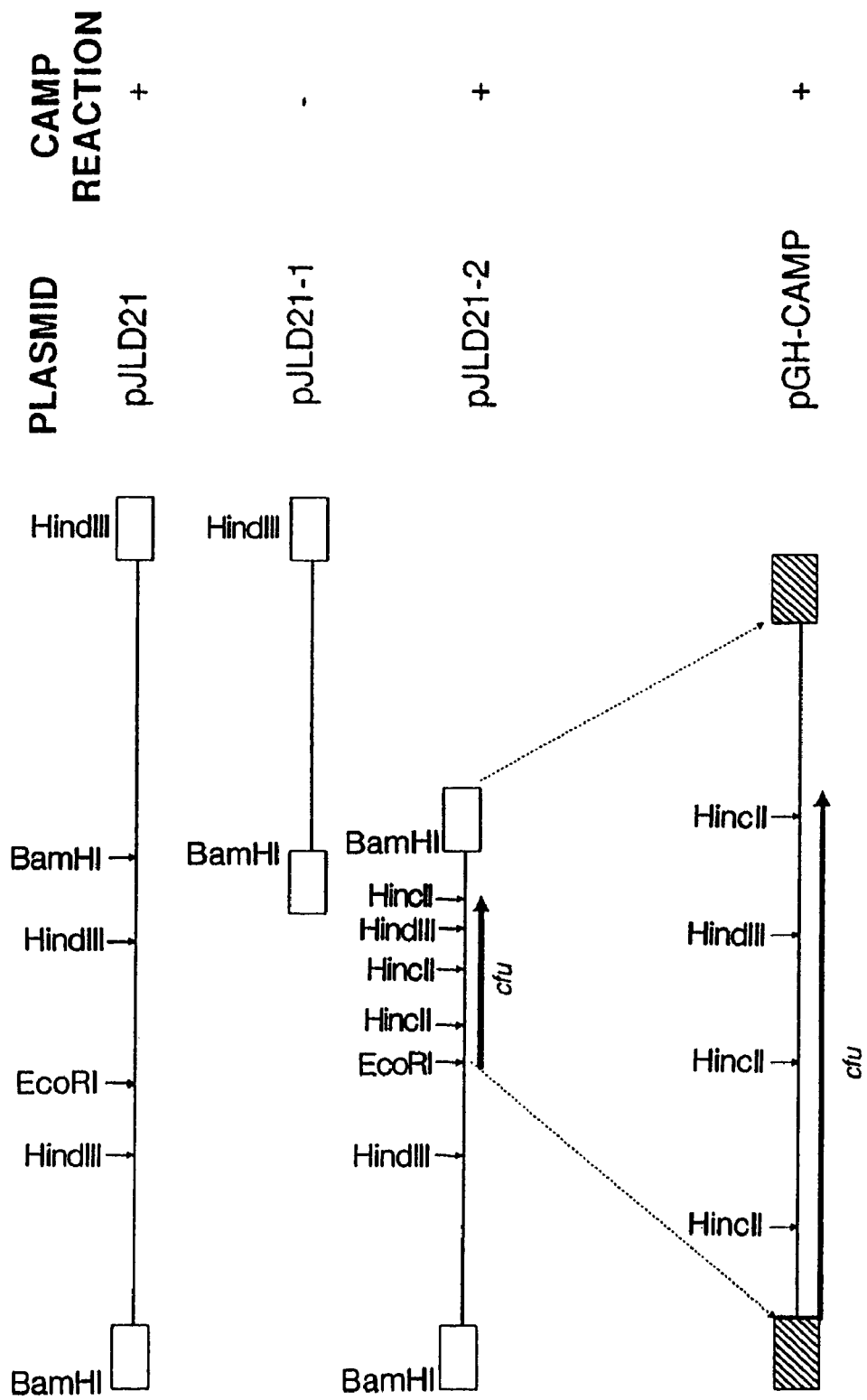
FIG. 5 depicts the construction of pGH-CAMP. The CAMP reactions for each clone from which the plasmid was derived are shown to the right of the figure; +indicates a positive reaction and –a negative reaction. Open boxes indicate pTZ18R and hatched boxes indicate pGH433.
Figure 7A:
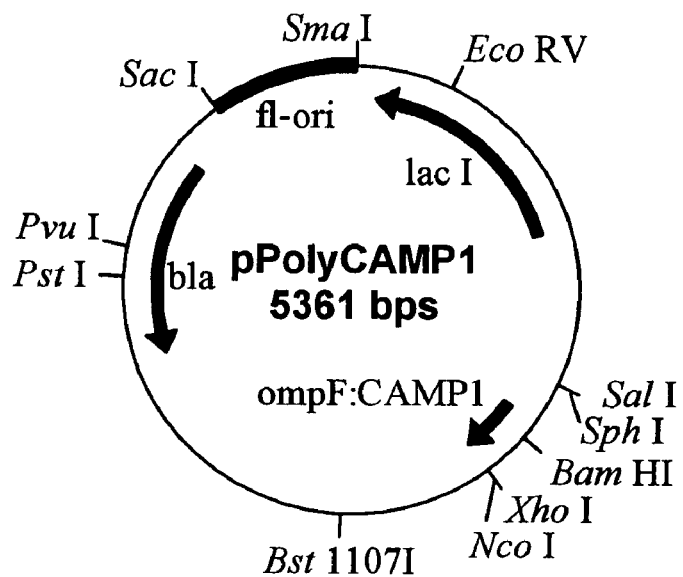
FIGS. 7A-7E show the plasmids used to construct the CAMP-3 chimera. The intermediate and final plasmids are shown. The restriction enzymes, location, and orientation of relevant genes are shown for each plasmid. The construction of these plasmids is explained in the experimental section.
Figure 7B:
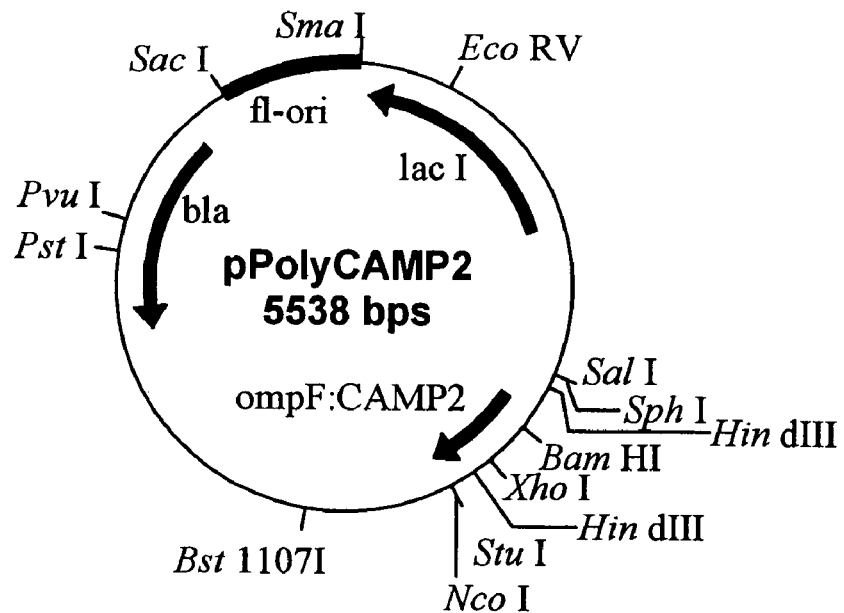
Figure 7C:
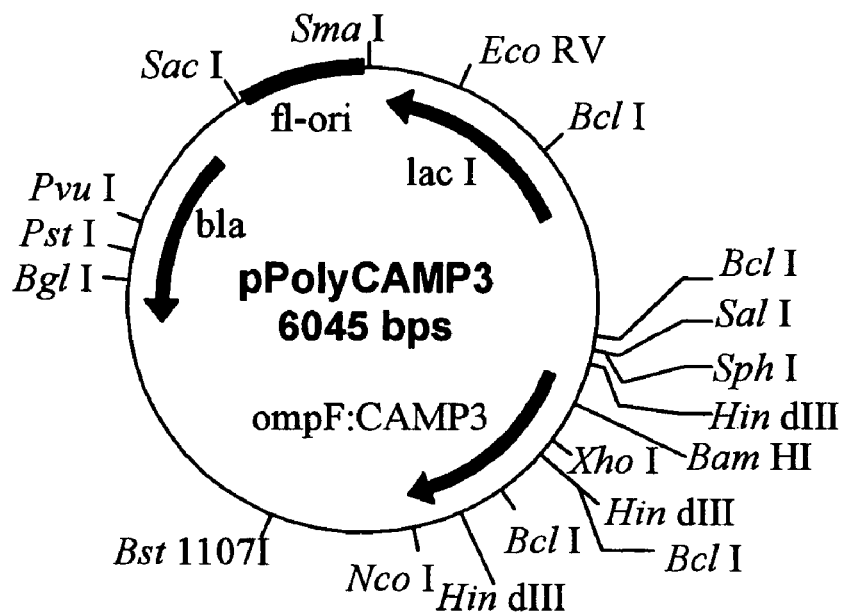
Figure 7D:
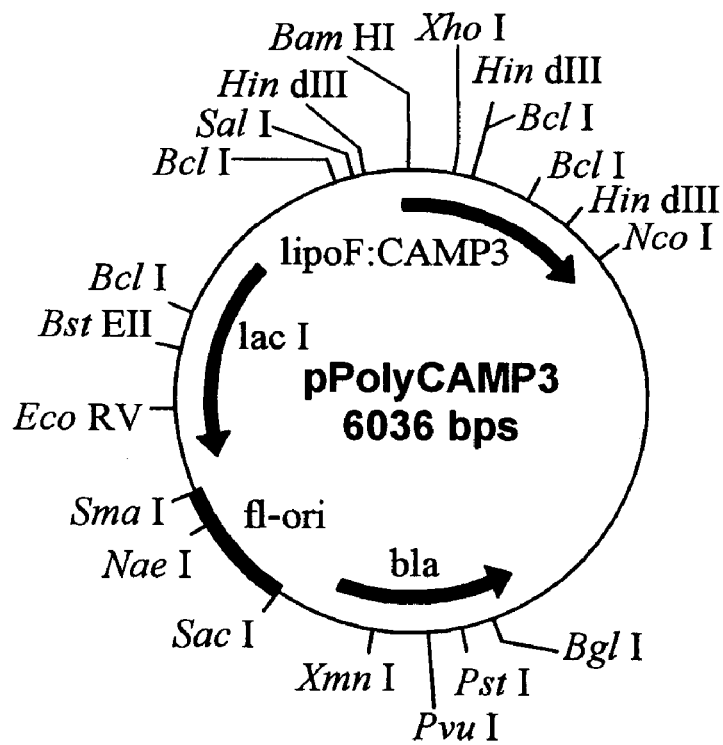
Figure 7E:
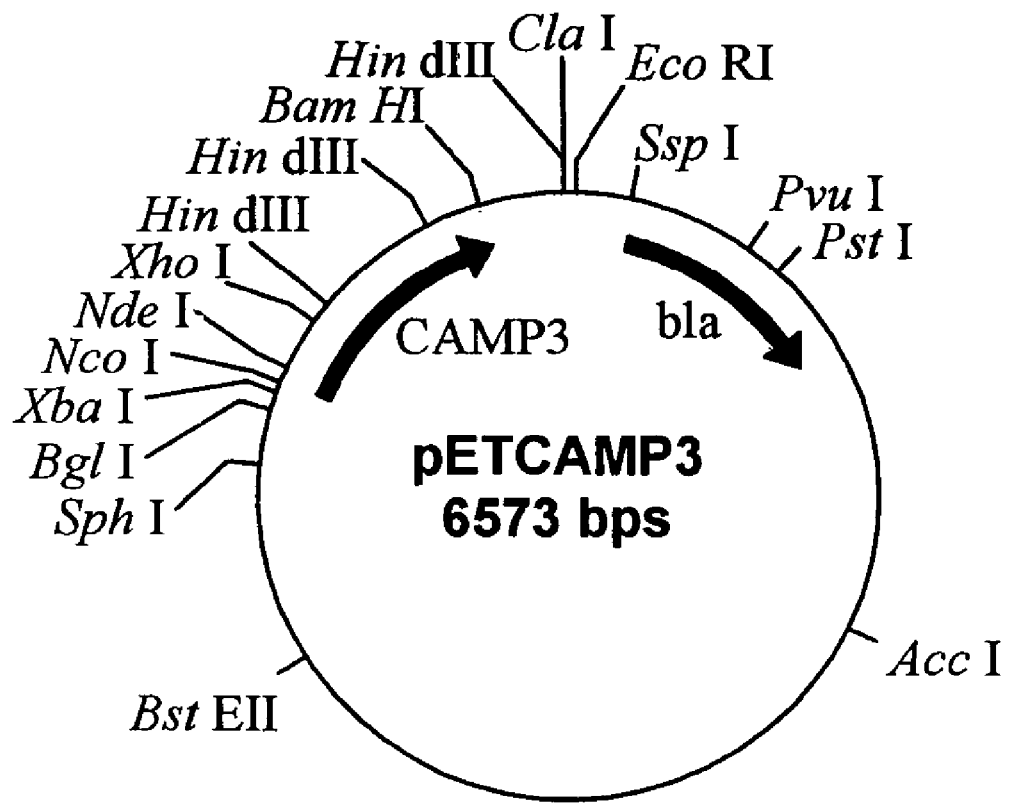

Another expression plasmid for the S. uberis CAMP factor, pGH-CAMP, was constructed as shown in FIG. 5. In particular, A 1.7 kb EcoRI-BamHI fragment of pJLD21-2 was filled in with Klenow polymerase and inserted into pGH433 which was cut by BamHI and filled in a similar fashion. Plasmid pGH433 is an expression vector containing a tac promoter, a translational start site with restriction enzyme sites allowing ligation in all three reading frames followed by stop codons in all reading frames. See, Theisen, M. and Potter, A. A. (1992) J. Bacteriol. 174:17-23.

The expression plasmids were used to transform E. coli JF1754 (described above). The CAMP factor was prepared from inclusion bodies as described in, e.g., Rossi-Campos et al. (1992) Vaccine 10:512-518, for use in the vaccine trials below. Briefly, bacteria were grown to mid-log phase and isopropyl-β,D-thiogalactoside (IPTG) was added and the cultures were incubated with vigorous agitation at 37° C. The bacteria were harvested by centrifugation, resuspended and frozen at −70° C. The frozen cells were thawed at room temperature and lysozyme was added. A detergent mix was then added. The viscosity was reduced by sonication and protein aggregates were harvested by centrifugation. The pellets were dissolved in a minimal volume of 4 M guanidine hydrochloride. The proteins were analyzed by sodium dodecyl sulfate-polyacrylamide gel electrophoresis and the protein concentration was estimated by comparing the intensity of the coomassie blue-stained bands to a bovine serum albumin standard.

EXAMPLE 2

Nucleotide Sequence of S. Uberis CAMP Factor Gene

To obtain the nucleotide sequence of the S. uberis CAMP factor gene, each of the EcoRI, HindIII, HincII and SacI fragments of pJLD21-2 was individually cloned into pTZ18R. Fragments were sequenced in both orientations as shown in FIG. 1. The coding sequence for the S. uberis CAMP factor, as well as the deduced amino acid sequence, is shown in FIG. 2 (SEQ ID NOS:1 and 2).

EXAMPLE 3

Comparison of the S. uberis CAMP Factor with S. Agalactiae CAMP Factor

To compare the S. uberis CAMP factor with protein B of S. agalactiae, a concentrated culture supernatant of S. agalactiae containing protein B (Jürgens et al. (1985) J. Chrom. 348:363-370) was separated by SDS-PAGE and analyzed by immunoblotting with antibodies against the purified S. uberis CAMP factor. A 25 kDa protein band from the S. agalactiae supernatant reacted in the immunoblot. This data indicated that monospecific antibodies raised against the S. uberis CAMP factor could cross-react with S. agalactiae protein B. This is not surprising since alignment of the amino acid sequence of the S. agalactiae CAMP factor with the deduced amino acids of the S. uberis CAMP factor showed 66.4% identical residues (FIG. 4).

EXAMPLE 4

Distribution of CAMP Factor Genes in Eight S. Uberis Strains

To study the distribution of the CAMP factor gene in other S. uberis strains, chromosomal DNA prepared from eight S. uberis strains was digested with the restriction endonuclease HindIII and separated on an agarose gel. Southern blot analysis with the 576 bp HindIII-EcoRI fragment of pJLD21 as a probe (FIG. 1) showed that a fragment identical in size to the HindIII fragment (1.2 kb) in pJLD21 was present in three S. uberis strains which were CAMP-reaction positive, while none of the CAMP reaction negative strains reacted with the probe. Thus, the CAMP-negative strains do not contain the cfu gene.

EXAMPLE 5

Immunogenicity and Protective Capability of the CAMP Factor

S. uberis CAMP factor, encoded by pGH-CAMP, was prepared from inclusion bodies as described in Example 1. The antigen was formulated in VSA3 adjuvant which is a combination of Emulsigen Plus™ from MVP Laboratories, Ralston, Nebr. and Dimethyldioctadecyl ammonium bromide (DDA) from Kodak (Rochester, N.Y.). The final concentration was 25 μg per ml of CAMP factor, 30% Emulsigen Plus, 0.9% Tween-80, and 2.5 mg per ml of DDA. The dose volume was 2 cc containing 50 μg of recombinant antigen.

Fifteen healthy lactating dairy cows from the Pennsylvania State University Mastitis Research Herd were used to study the ability of the S. uberis CAMP factor to protect cows from mastitis. Animals were assigned to two groups of five cows. Treatment groups consisted of 1) experimental, given the vaccine including the S. uberis CAMP factor, administered intramuscularly at dry off and again 28 days later, and 2) placebo (vehicle) administered via intramuscular injection at dry off and again 28 days later.

All animals were challenged in one quarter with S. uberis on day four of lactation. Milk and blood samples were obtained as outlined in Table 1.

TABLE 1

Sampling Schedule

| TIME | SAMPLE |
| --- | --- |
| dry off, D − 0 | serum, milk, immunization |
| 14 days dry, D + 14 | serum |
| 28 days dry, D + 28 | serum, immunization |
| 52 days dry, D + 52 | serum |
| calving, C − 0 | serum, milk, bacteriology |
| 4 days lactation, CH − 0 | serum, milk, bacteriology, challenge |
| 5 days lactation, CH + 1 | bacteriology |
| 6 days lactation, CH + 2 | bacteriology |
| 7 days lactation, CH + 3 | serum, milk, bacteriology |
| 14 days lactation, CH + 10 | serum, milk, bacteriology |
| 21 days lactation, CH + 17 | serum, milk, bacteriology |

The challenge strain of S. uberis (ATCC strain 9927) was obtained from a clinical case of bovine mastitis. The stock culture of S. uberis was grown in tryptic soy broth and individual aliquot were stored at −70° C. on blood beads until needed. The bacterial challenge was prepared by rolling the stock bead cultures onto esculin blood agar plates containing 5% whole blood. After 24 hours incubation at 37° C., a single colony was used to inoculate 100 ml of Ultra High Temperature pasteurized (UHT) milk and incubated for 12 hours at 37° C. The 24 hour culture was mixed well and a 100 µl aliquot was removed to inoculate a second 100 ml of UHT milk. After a second 9 hour incubation at 37° C., the culture was serially diluted in 10-fold increments using sterile saline. The colony forming units (CFU) per ml of each dilution was determined by absorbance on a spectrophotometer and confirmed by plate pouring onto blood agar plates. The dilution containing 200 CFR of S. uberis per ml of saline was selected for each challenge.

Total Ig titers for CAMP factor were determined by an indirect ELISA. Immunlon-2 plates were coated with antigen in carbonate buffer. Prior to use, the plates were blocked with TBST (100 mM Tris Cl, pH 8.0; 150 mM NaCl; 0.05% Tween-20) and 3% BSA for 1 hour. After blocking, the plates were washed with distilled water. Serum and milk samples were serially diluted in 3-fold increments using TBST containing 1% BSA. Rabbit antisera for S. uberis CAMP factor was also diluted and served as a positive control. Negative control samples contained TBST with 1% BSA. The diluted samples and controls were transferred to the coated plates and were incubated for 1 hour at room temperature. The plates were washed thoroughly with distilled water and all wells were incubated with a horse radish peroxidase conjugate of goat anti-IgG diluted 1:2000 in TBST containing 1% BSA. Following a 1 hour incubation at room temperature, the plates were washed with distilled water. The amount of antibody present in samples was visualized using ABT substrate. The titers of each sample were based on the absorbance reading at 405 nm with a reference wavelength of 495 nm. A positive reading for samples was one in which the absorbance was two times the absorbance of the blank (negative control). Titers were determined by taking the reciprocal of the last dilution giving a positive reading. Consistency among assay plates was monitored by the absorbance reading of positive controls.

The results are shown in TABLES 2 and 3. As can be seen, antibody titers were greater in the vaccinated animals than in the placebo group.

TABLE 2

Average Serum Titers Following Experimental Challenge with S. uberis

| Treatment Group | Before Immunization | Before Challenge | After Challenge |
|---|---|---|---|
| Placebo A[1] | 6.75 | 45.0 | 45.0 |
| CAMP factor | 3.00 | 819.00 | 445.50 |

[1]Serum titers of samples obtained from placebo immunized animals screened for CAMP factor.

TABLE 3

Average Lacteal Antibody Titers Following Experimental Challenge with S. uberis

| Treatment Group | Before Immunization | Before Challenge | After Challenge |
|---|---|---|---|
| Placebo A[1] | 0.00 | 0.00 | 1.33 |
| CAMP factor | 8.00 | 288.00 | 42.50 |

[1]Lacteal antibody titers of samples obtained from placebo immunized animals screened for CAMP factor.

Somatic cell counts are a traditional measure of mastitis in cows. Accordingly, milk was assayed for somatic cells using standard assay. Results are shown in TABLE 4. As is readily apparent, immunized animals had a somatic cell count within normal limits while the placebo group had cell counts indicating the presence of mastitis. Thus, the CAMP factor vaccine was effective in preventing mastitis.

TABLE 4

Average Milk Somatic Cell Counts Following Experimental Challenge with S. uberis

| Treatment Group | Before Challenge[1] | After Challenge[2] |
|---|---|---|
| | 1000 cells/ml milk | |
| Placebo A | 130.50 | 2825.25 |
| CAMP factor | 251.75 | 51.50 |

[1]Milk SCC obtained from quarters immediately prior to intramammary challenge with S. uberis
[2]Milk SCC obtained from quarters 3 days following intramammary challenge with S. uberis

EXAMPLE 6

Cloning, Expression and Purification of a Chimeric CAMP Factor Construct

A chimeric CAMP protein (CAMP-3) comprising epitopes from the S. uberis and S. agalactiae CAMP factors, was constructed in order to provide a highly immunogenic, cross-reactive vaccine antigen. FIG. 7 shows the intermediate and final plasmids used to construct the CAMP-3 chimera. The DNA and amino acid sequences of the final construct are shown in FIG. 8. The construct includes DNA encoding amino acids 31-87 of the S. agalactiae sequence shown in FIG. 3, cloned between those encoding $Leu_{90}$ and $Lys_{91}$ residues of S. uberis CAMP.

The published nucleotide sequences of the CAMP-encoding genes cfb (Podbielski et al. (1994) Med. Microbiol. Immunol. 183:239-56 and cfx (Jiang et al. (1996) Microbiol. Path. 20:297-307), from S. agalactiae and S. uberis respectively, were used to design PCR primers (shown in Table 5), allowing construction of the chimeric CAMP-encoding gene, camp-3. A PCR fragment encoding amino acid residues 30-90 of cfx was amplified with the primers CAMP-1 and CAMP-2. The fragment was cloned into the expression vector pAA556a (which contains OmpF-terminal-encoding sequences, directing export of OmpF fusion proteins to the E. coli cell surface) using the primer encoded BamHI and NdeI restriction sites, and the resulting construct was designated pPolyCAMP-1. A second PCR fragment, encoding residues 31-87 of cfb, was amplified with the primers CAMP-3 and CAMP-4 and cloned into pPoly-CAMP-1 using XhoI and NcoI sites to give pPolyCAMP-2. Finally, a third PCR fragment, encoding residues 91-258 of cfx, was amplified with the primers CAMP-5 and CAMP-6 and digested with Eco47-3 and NcoI. This fragment was cloned into StuI/NcoI digested pPolyCAMP-2, and the resulting construct, pPoly-CAMP-3, contained a chimeric gene, camp-3, encoding a protein of 317 aa, with a calculated $M_r$ of 34,956 Da and a pI of 5.5. This protein is the CAMP-3 chimera fused to the LipoF signal sequence. The camp-3 construct was sequenced in both directions using the primers 556-1 and 556-2. The DNA ing conditions using metal chelate chromatography. Thus, the final construct, plasmid pET-CAMP3, encoded a (6xHis) CAMP-3 fusion protein. DNA sequence analysis of this construct revealed that the CAMP-3 ORF was not fused to the peptide encoding the histidine tag, but that its expression was still controlled by IPTG. This construct was used to transform *E. coli* strains, described above, using the polyethylene glycol method (Kurien and Scofield (1995) *BioTechniques* 18: 1023-1026) or by repeated washes of the cells in sterile-distilled water as previously described (Frohelich and Scott (1991) *Gene* 108:99-1.01).

TABLE 5

PCR and sequencing primers

| Primer | Sequence | | Comments |
|---|---|---|---|
| CAMP-1 | 5'-AAAAAAGGATCCAATCAAATAAA TGTTAGTCAACCA-3' | (SEQ ID NO: 10) | Forward primer, annealing to nt 91-112 of the *S. uberis* CAMP coding sequence. BamHI site underlined. |
| CAMP-2 | 5'-AAAAACCATGGCTACTCGAGATTTT CAACAGCTGAATTGCTG AATTAAC-3' | (SEQ ID NO: 11) | Reverse primer, annealing to nt 267-238 (opposite strand) of the *S. uberis* CAMP coding sequence. XhoI, and NcoI underlined. |
| CAMP-3 | 5'-AAAAACTCGAGCAAGTGACAACT CCACAAGTGG-3' | (SEQ ID NO: 12) | Forward primer, annealing to nt 91-102 of the *S. agalactiae* CAMP coding sequence. XhoI site underlined. |
| CAMP-4 | 5'-AAAAAACCATGGCTAAGGCCTTAAT TTTTCCACGCTAGTAATAGCCTC-3' | (SEQ ID NO: 13) | Reverse primer, annealing to nt 261-235 (opposite strand) of the *S. agalactiae* CAMP coding sequence. StuI, and NcoI sites underlined. |
| CAMP-5 | 5'-AAAAAAGCGCTAAAACTTCACTTA GAGCTAATCCTG-3' | (SEQ ID NO: 14) | Forward primer, annealing to nt. 271-295 of the *S. uberis* CAMP coding sequence. Eco47-3 site underlined. |
| CAMP-6 | 5'-AAAAACCATGGTCATTACTGTAGAG CAGTATTTAATGCTTC-3' | (SEQ ID NO: 15) | Reverse primer, annealing to nt 777-751 (opposite strand) of the *S. uberis* CAMP coding sequence. NcoI site underlined. |
| His-CAMP-1 | 5'-AAAAAACATATGTCCAATCAAATAA ATGTTAGTCAACC-3' | (SEQ ID NO: 16) | Forward primer for cloning into pET-15b. NdeI site underlined. |
| His-CAMP-2 | 5'-TTTTTGGATCCTTACTGTAGAGCAGT ATTTAATGC-3' | (SEQ ID NO: 17) | Reverse primer for cloning into pET-15b. BamHI site underlined. |
| 556-1 | 5'-GTGTGGAATTGTGAGCGG-3' | (SEQ ID NO: 18) | Forward primer for sequencing of cloned inserts in pAA556a, annealing to nt 1791-1808. |
| 556-2 | 5'-CTCCCTGCCTCTGTC-3' | (SEQ ID NO: 19) | Reverse primer for sequencing of cloned inserts in pAA556a, annealing to nt 1979-1965 (opposite strand). | sequence of the chimeric construct was determined using an ABI 373 DNA automatic sequencer (Applied Biosystems). The DNA sequence and corresponding amino acid sequence of the CAMP-3 chimera is shown in FIG. 8 at DNA positions 79-942 (amino acid positions 27-314). Nucleotide positions 1-78 (amino acid positions 1-26) represent the LipoF signal sequence.

To provide enough pure protein for subsequent vaccine studies, an NdeI/BamHI fragment containing the camp-3 region of pPolyCAMP-3, minus the OmpF signal sequence, was cloned into the expression vector pET15b (Novagen, Madison, Wis.) which had been digested with BamHI and NdeI. Cloning of the PCR product into this site results in the addition of an in-frame coding sequence for a hexahistidyl (6xHis) tag to the CAMP coding sequence. Subsequent expression yields a protein with an attached histidine tag, which permits purification of the protein under non-denatur- The CAMP-3 protein was purified by anion exchange chromatography of a filtered lysate of an IPTG-induced culture of BL21 (DE3) containing pET-CAMP3. Cells were collected by centrifugation at 6,000×g for 10 min at 4° C., washed in 0.1 M PBS (pH 7.2), and disrupted by sonication. The volume of the soluble fraction was adjusted to 650 ml with 20 mM $Na_2HPO_4$ (pH 7.5), and filtered through a 0.22 μm filter (Millipore). Q-sepharose fast flow anion exchange resin was packed into an XK26/20 column to a bed height of 13 cm (70 ml column volume). The column was equilibrated with buffer A (20 mM $Na_2HPO_4$, pH 7.5), and the protein solution was passed through at a rate of 7 ml/min. The column was washed with 7.4 column volumes (CV) of buffer A, and protein was eluted with a gradient buffer (0% buffer A-50% buffer B [buffer A+1 M NaCl, pH 7.5] over 12.85 CV and from 50-100% buffer B in 3.6 CV, and finally 100% of buffer B for 1.7 CV). The column eluate was monitored at 260 nm, and fractions were concentrated with BIOMAX-30 K filters. Analysis by SDS-PAGE and Western blot determined that the CAMP-3 protein eluted in the breakthrough and buffer A fractions. Densitometry of SDS-PA gels estimated protein purity to be >60%.

EXAMPLE 7

Immunization and Challenge of Lactating Cows with Chimeric CAMP Factor

Experiments to test the effectiveness of vaccines comprising the chimeric CAMP factor, as well as the *streptococcal* protein, GapC, from *S. uberis* and *S. dysgalactiae*, were conducted in lactating cows as follows. A total of 99 lactating Holstein cows were screened for the presence of serum IgG against *S. uberis* whole cells, GapC and CAMP. Four groups of 8 animals were selected for vaccination with a placebo, (6×His)GapC of *S. uberis*, (6×His)GapC of *S. dysgalactiae* and CAMP-3. Each vaccine dose (2 ml) included 100 μg/ml of purified (6×His)GapC, CAMP-3 or antigen-free placebo (0.85% (w/v) saline), and 30% VSA3 (VIDO, Saskatoon, Saskatchewan, Canada; van Drunen Littel-van den Hurk et al. (1993) *Vaccine* 11:25-35). Cows received 2 subcutaneous injections in the neck at 36 (day 0) and 15 days prior to challenge. Eight days before challenge, milk samples from each quarter were analysed for the presence of bacteria, and infected animals were excluded from the trial. Subsequently, 6 cows from each group were challenged. Three hrs before challenge, teats were washed with clean, warm water, dried, and alcohol swabbed. Milk samples were collected for somatic cell counts (SCC) and bacteriology. The left udder quarters remained unchallenged as controls. Three ml of inoculum was administered by intramammary infusion to the right quarters of each animal, containing $3.0 \times 10^7$ cfu/ml of an exponential-phase culture of *S. uberis* SU21 (clinical isolate obtained from Animal Health Laboratory, Alberta, Canada) suspended in 0.85% (w/v) saline. Milk samples were collected from all quarters, daily for 7 days post-challenge, for determination of SSC and bacteriology. All samples were stored on ice, and analysed within 48 hrs of collection. Clinical assessments of animals included measurement of rectal temperatures, and udder swelling (visual and palpated). A numerical score of 1 (normal) to 3.5 (severe mastitis) was assigned to each animal and used as a means of comparing the severity of mastitis among vaccine groups. Milk quality was assessed by the presence of clots.

Serum IgG titers were determined at the time of first and second vaccinations, at 8 days before challenge (day 28), and at 11 days post-challenge (day 47). Similarly, milk IgG titers were determined at day 21 and 43. Serum IgA titers were determined at day 21 and 47, and milk IgA titers were determined at day 21 and 43. Round-bottomed, 96-well microtiter plates (Nunc) were coated overnight at 4° C. with CAMP-3, and (6×His)GapC of *S. uberis* and *S. dysgalactiae* (100 ng/well in 100 μl of carbonate buffer, pH 9.6), and blocked for 1 hr at 37° C. with 200 μl of PBSTg. 100 μl of test sample was added/well, and plates were incubated for 2 hrs at room temperature. After washing, alkaline phosphatase-conjugated goat anti-bovine IgG (H & L; Kirkegaard and Perry Labs. Inc., Gaithersburg, Md.) was added (100 μl/well), and plates were incubated for 1 hr at room temperature. Plates were washed, and alkaline phosphatase activity was detected at 405 nm following incubation with p-nitrophenyl phosphate in 1 M diethanolamine (pH 9.8) and 0.5 mM $MgCl_2$ for 1.5 hrs at room temperature.

Determination of milk IgG and IgA was carried out after treating milk with a commercially available rennin solution, as follows: one tablet of Rennet (CHR HANSEN) was dissolved in 40 ml of $H_2O$, and 0.1 ml of this solution was added to 2 ml of milk and incubated at room temperature for 4 hrs. Coagulated casein was pelleted by centrifugation at 3,000×g for 20 min, and the middle layer was removed (the top layer comprised fat) and analysed as for serum samples. Both serum and milk titers were determined by the intersection of the least-square regression of the $OD_{405}$ versus logarithm of dilution with the $OD_{405}$ obtained from wells containing no serum.

Determination of SCC from milk samples was carried out at the Pacific Milk Analysis Laboratory (Chilliwak, British Columbia). Samples were collected in 14 ml polystyrene, round-bottomed tubes (Falcon) containing a preservative. SCC were fixed by mixing 0.5 ml of milk samples with 10 μl of fixative liquid (0.2 mg/ml eosine, 3.3% formaldehyde solution) for 18 hrs at 30° C. Samples were diluted 1/100 in emulsifier electrolyte solution (12% ethanol, 0.02% Triton X-100, 0.1 M NaCl), and incubated at 80° C. for 10 min. After cooling to room temperature, SCC were determined with a Coulter counter. Repeated measures analysis of variance of SCC among treatments, and over time, was performed using the SYSTAT 10 software package (SPSS Science, Chicago, USA).

Table 6 shows pre- and post-challenge titers, presented as the arithmetic means of the natural log transformed values of serum titers from all animals in each treatment group (standard deviations in parentheses). Prior to vaccination, only 4 animals showed any detectable serum IgG titer against (6×His)GapC. Following vaccination, all animals vaccinated with (6×His)GapC showed a significant increase in both serum and milk anti-(6×His)GapC IgG titers, which consistently remained at least 10-fold higher than the control animals, while anti-(6×His)GapC IgG titers in animals vaccinated with CAMP-3 were similar to those of the control group. Anti-(6×His)GapC IgG titers in milk were consistently lower than the corresponding values in serum. However, immediately prior to challenge the increased serum and milk IgG titers in (6×His)GapC vaccinated animals, compared to control and CAMP-3 vaccinated animals, was apparent. Serum anti-(6×His)GapC IgA levels were detectable in all groups prior to challenge, but rose significantly following challenge. Even the CAMP-3 vaccinated group showed an increase in serum anti-(6×His)GapC IgA titers, most likely resulting from exposure to the cell surface-associated GapC of the *S. uberis* challenge bacteria. In CAMP-3 vaccinated animals, a post-challenge increase in anti-(6×His)GapC milk IgG titers was also observed, although a corresponding increase was not observed in serum IgG titers. In contrast to serum, milk anti-(6×His)GapC IgA was virtually undetectable in all groups, both pre- and post-challenge.

Following vaccination of cows with CAMP-3, there was a marked increase in serum and milk anti-CAMP IgG titers, compared to those of the control and (6×His)GapC vaccinated animals. Furthermore, in contrast to anti-(6×His)GapC IgG titers, anti-CAMP-3 titers increased post-challenge, whereas those for (6×His)GapC decreased slightly. Although the cause is unknown, this observation was consistent throughout all vaccine groups; post-challenge serum anti-(6× His)GapC IgG titers were found to have decreased, whereas the corresponding titers in milk had increased (with the exception of the *S. dysgalactiae* (6×His)GapC vaccinated group). Pre-challenge, serum anti-CAMP-3 IgA titers were higher than the equivalent serum anti-(6×His)GapC titers determined at the same time point (day 21), and at the time the post-challenge serum samples were taken, anti-CAMP-3 IgA levels had increased in all groups, most significantly in those vaccinated with CAMP-3. In contrast, both pre- and post-challenge milk anti-CAMP-3 IgA titers were virtually undetectable.

Following challenge with *S. uberis* SU21, at no point were bacteria recovered from any animals, vaccinated or otherwise. This is consistent with the results of a previous study (Finch et al. (1994) *Infect. Immun.* 62:3599-3603), where no bacteria were isolated following challenge from dairy cows vaccinated with heat-killed *S. uberis*, although bacteria were isolated from the unvaccinated control animals. It is possible that in the current study the inoculum administered was low enough to induce mastitis without causing persistent infection, even in unvaccinated animals. However, despite the absence of recoverable bacteria, animals did display clinical signs of disease, and SCC indicated that inflammation had occurred. Therefore, the challenge was deemed successful. Between vaccine groups, no significant differences were observed in rectal temperatures, and clinical scores determined that there were no significant differences in the severity of infection. Although no differences in milk yield were observed in any animals, the quality of milk was slightly affected in all groups, as discussed below.

Figure 9:
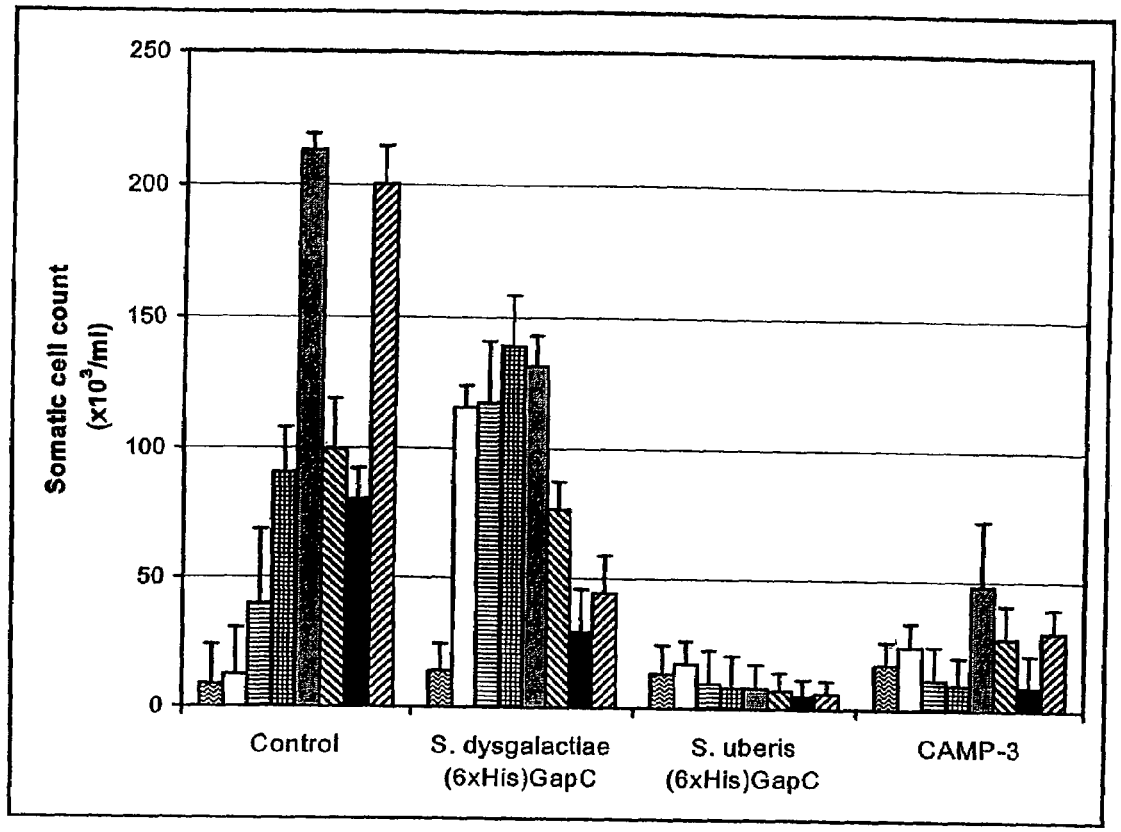
FIG. 9 shows the geometric mean SCC (plus 1 standard deviation) in quarters challenged with *S. uberis* in groups of cows as described in the examples, for 7 days following challenge. Data sets correspond to day 0 (the far left bar), day 1 (the second bar from the left), day 2 (the third bar from the left), day 3 (the fourth bar from the left), day 4 (the fifth bar from the left), day 5 (the sixth bar from the left), day 6 (the seventh bar from the left), and day 7 (the eighth bar from the left). Despite the appearance of the figure, the SCC for *S. dysgalactiae* (6×His)GapC vaccinated animals on days 7 and 8, and CAMP-3 vaccinated animals on days 4 and 5 post-challenge were not statistically significantly different from those of the control.

The bovine udder is comprised of unconnected quarters, and by challenging only 2 quarters with *S. uberis* an internal control was provided for each animal. FIG. 9 shows SCC over the course of the trial, for each particular vaccine group. On initial analysis, the reported SCC of the control group appeared somewhat variable; however, the overall relationship was an increase of SCC over time, explained by a quadratic relationship ($p=0.02$). After day 2, SCC of the control group increased markedly, reaching their highest level at day 4 post-challenge. SCC then decreased slightly, before rising markedly again by day 7 post-challenge. This somewhat erratic trend is consistent with SCC values reported elsewhere, following challenge of lactating cows with *S. uberis* (Finch et al. (1997) *Vaccine* 15:1138-1143; Finch et al. (1994) *Infect. Immun.* 62:3599-3603). The SCC of *S. dysgalactiae* (6×His)GapC vaccinated animals increased sharply immediately post-challenge, reaching a maximum at day 3, before decreasing erratically over the remainder of the trial. Nevertheless, at no point was the decrease in SCC statistically significantly different from that of the control group, despite an apparent difference from day 4 post-challenge onward. This result may be because the *S. dysgalactiae* (6×His)GapC is not as protective as that of *S. uberis*.

Vaccination with *S. uberis* (6×His)GapC resulted in a significant decrease in SCC, compared to the control group. From day 3 onward, SCC in this group were statistically significantly lower than those of the control group (p values of 0.023 at day 3, 0.001 at day 4, 0.011 at day 5, 0.006 at day 6, and 0.000 at day 7 post-challenge). SCC of cows vaccinated with the CAMP-3 antigen were slightly higher than those of the *S. uberis* (6×His)GapC vaccinated animals, although they were still clearly lower than those of the control group. Comparison of SCC of the control and CAMP-3 vaccinated groups revealed statistically significant differences at days 3 (p value of 0.033), 6 and 7 post-challenge (p values of 0.032, and 0.046 respectively), but not at days 4 and 5, even though SCC were obviously lower in the CAMP-3 vaccinated group on these days.

Following challenge with SU21, the time that milk quality remained affected varied between vaccine groups. Post-challenge, milk quality in the control, *S. dysgalactiae* (6×His)GapC, CAMP-3, and *S. uberis* (6×His)GapC vaccinated groups was reduced for a total of 21, 24, 11, and 9 days respectively. According to this data, mastitis in the *S. dysgalactiae* (6×His)GapC vaccinated group was no less severe, if not worse, than that of the control group. Conversely, although vaccination with *S. uberis* (6×His)GapC did not completely prevent reduced milk quality, it did significantly reduce the length of time that milk quality was affected. Vaccination with CAMP-3 also appeared to reduce the length of time that milk quality was reduced, although not as much as in the *S. uberis* (6×His)GapC group, which is in keeping with the SCC results.

TABLE 6

Anti-GapC and anti-CAMP IgG and IgA titers[a]

| Antigen | | Group | IgG titers | | IgA titers | |
|---|---|---|---|---|---|---|
| | | | Serum | Milk | Serum | Milk |
| GapC | Pre-challenge | 1 | 8.33 (±0.87) | 4.28 (±0.55) | 2.75 (±0.85) | 0.86 (±1.10) |
| | | 2 | 12.74 (±1.64) | 7.12 (±0.34) | 3.39 (±0.31) | 2.11 (±1.22) |
| | | 3 | 13.21 (±0.84) | 7.85 (±1.09) | 2.72 (±1.50) | 1.24 (±1.33) |
| | | 4 | 9.41 (±0.69) | 4.51 ± 0.61 | 2.09 (±1.03) | 1.34 (±1.26) |
| | Post-challenge | 1 | 2.42 (±3.75) | 6.38 (±0.55) | 4.20 (±0.97) | 1.35 (±1.55) |
| | | 2 | 10.12 (±1.34) | 6.66 (±0.22) | 4.78 (±0.94) | 1.14 (±1.25) |
| | | 3 | 10.79 (±1.07) | 9.05 (±1.64) | 4.64 (±1.02) | 1.31 (±1.22) |
| | | 4 | 5.30 (±4.14) | 5.84 (±0.46) | 3.49 (±3.28) | 1.80 (±1.25) |
| CAMP | Pre-challenge | 1 | 7.35 (±1.00) | 4.06 (±0.39) | 1.63 (±1.53) | 0.60 (±0.81) |
| | | 2 | 7.98 (±0.98) | 5.33 (±0.34) | 0.90 (±1.36) | 1.77 (±0.90) |
| | | 3 | 7.21 (±0.99) | 5.06 (±0.70) | 2.56 (±1.90) | 1.67 (±1.42) |
| | | 4 | 11.82 (±0.59) | 8.37 (±1.02) | 3.69 (±2.31) | 1.46 (±1.44) |
| | Post-challenge | 1 | 6.19 (±4.82) | 4.87 (±1.37) | 0 | 0.58 (±0.94) |
| | | 2 | 6.98 (±3.52) | 5.07 (±0.78) | 1.46 (±2.42) | 0.41 (±0.99) |
| | | 3 | 6.41 (±5.24) | 5.26 (±1.00) | 2.66 (±2.24) | 1.85 (±1.42) |
| | | 4 | 13.47 (±0.55) | 8.90 (±1.13) | 5.09 (±1.42) | 1.90 (±1.30) |

[a]Groups shown are 1. Control, 2. *S. dysgalactiae* (6×His)GapC, 3. *S. uberis* (6×His)GapC, and 4. CAMP-3 vaccinates. Pre-challenge data correspond to serum IgG titers at day 28, and serum IgA, milk IgG and IgA titers at day 21. Post-challenge data correspond to serum IgG titers at day 47, and serum IgA, milk IgG and IgA titers at day 43.

Thus, immunogenic CAMP factors are disclosed, as are methods of making and using the same. Although preferred embodiments of the subject invention have been described in some detail, it is understood that obvious variations can be made without departing from the spirit and the scope of the invention as defined by the appended claims.

The invention claimed is:

1. A polynucleotide comprising a coding sequence encoding an immunogenic polypeptide, wherein said coding sequence encodes a polypeptide comprising the amino acid sequence depicted at positions 27-314 of SEQ ID NO: 9.

2. The polynucleotide of claim 1, wherein the immunogenic polypeptide further comprises a signal sequence.

3. The polynucleotide of claim 2, wherein said signal sequence comprises the sequence of amino acids depicted at positions 1-26 of SEQ ID NO: 9.

4. The polynucleotide of claim 1, wherein the coding sequence encodes an immunogenic polypeptide comprising the amino acid sequence depicted in SEQ ID NO: 9.

5. A recombinant vector comprising:
(a) the polynucleotide of claim 1; and
(b) at least one control element operably linked to said polynucleotide, whereby said coding sequence can be transcribed and translated in a host cell.

6. A recombinant vector comprising:
(a) the polynucleotide of claim 2; and
(b) at least one control element operably linked to said polynucleotide, whereby said coding sequence can be transcribed and translated in a host cell.

7. A recombinant vector comprising:
(a) the polynucleotide of claim 3; and
(b) at least one control element operably linked to said polynucleotide, whereby said coding sequence can be transcribed and translated in a host cell.

8. A recombinant vector comprising:
(a) the polynucleotide of claim 4; and
(b) at least one control element operably linked to said polynucleotide, whereby said coding sequence can be transcribed and translated in a host cell.

9. A host cell comprising the recombinant vector of claim 7.

10. A host cell comprising the recombinant vector of claim 6.

11. A host cell comprising the recombinant vector of claim 8.

12. A method for producing an immunogenic polypeptide, said method comprising culturing a population of host cells according to claim 10 under conditions for producing said polypeptide.

13. A method for producing an immunogenic polypeptide, said method comprising culturing a population of host cells according to claim 9 under conditions for producing said polypeptide.

14. A method for producing an immunogenic polypeptide, said method comprising culturing a population of host cells according to claim 11 under conditions for producing said polypeptide.

* * * * *

SEQUENCE LISTING

<160> NUMBER OF SEQ ID NOS: 19

<210> SEQ ID NO 1
<211> LENGTH: 777
<212> TYPE: DNA
<213> ORGANISM: Artificial Sequence
<220> FEATURE:
<223> OTHER INFORMATION: Description of Artificial Sequence: S. uberis
      CAMP factor
<220> FEATURE:
<221> NAME/KEY: CDS
<222> LOCATION: (1)..(777)

<400> SEQUENCE: 1

```
atg ctt atg gaa ttc aaa aag tta ctt tat tta act ggt tca atc gca      48
Met Leu Met Glu Phe Lys Lys Leu Leu Tyr Leu Thr Gly Ser Ile Ala
  1               5                  10                  15 gga att act tta ttt tcc cca att tta aca agt gtc caa gca aat caa      96
Gly Ile Thr Leu Phe Ser Pro Ile Leu Thr Ser Val Gln Ala Asn Gln
             20                  25                  30 ata aat gtt agt caa cca tct aat aat gaa agt aat gtt att tca cag     144
Ile Asn Val Ser Gln Pro Ser Asn Asn Glu Ser Asn Val Ile Ser Gln
         35                  40                  45 aaa aaa gaa gaa att gat aat agt cta aat cag gaa agt gct caa cta     192
Lys Lys Glu Glu Ile Asp Asn Ser Leu Asn Gln Glu Ser Ala Gln Leu
     50                  55                  60 tat gcc ttg aaa gaa gat gtt aaa gga act gag aaa gaa caa tca gtt     240
Tyr Ala Leu Lys Glu Asp Val Lys Gly Thr Glu Lys Glu Gln Ser Val
 65                  70                  75                  80 aat tca gca att tca gct gtt gaa aat tta aaa act tca ctt aga gct     288
Asn Ser Ala Ile Ser Ala Val Glu Asn Leu Lys Thr Ser Leu Arg Ala
                 85                  90                  95 aat cct gaa aca att tat gat tta aat tcg att gga aca aga gta gaa     336
Asn Pro Glu Thr Ile Tyr Asp Leu Asn Ser Ile Gly Thr Arg Val Glu
            100                 105                 110 gca atc tct gac gtg att caa gca att gtt ttt tca acg caa cag tta     384
Ala Ile Ser Asp Val Ile Gln Ala Ile Val Phe Ser Thr Gln Gln Leu
        115                 120                 125 aca aat aaa gtt gat caa gct cac att gat atg gga ttt gct att acg     432
Thr Asn Lys Val Asp Gln Ala His Ile Asp Met Gly Phe Ala Ile Thr
    130                 135                 140 aaa tta ctt att cgc att gca gac cca ttt gct tca aat gaa tcc att     480
Lys Leu Leu Ile Arg Ile Ala Asp Pro Phe Ala Ser Asn Glu Ser Ile
145                 150                 155                 160 aaa ggg caa gtc gaa gct gtt aaa caa gtg caa gcg act gtg ctt acc     528
Lys Gly Gln Val Glu Ala Val Lys Gln Val Gln Ala Thr Val Leu Thr
                165                 170                 175 tat ccc gat ttg cag cct acg gat aga gca act att tac gtt aaa tca     576
Tyr Pro Asp Leu Gln Pro Thr Asp Arg Ala Thr Ile Tyr Val Lys Ser
            180                 185                 190 aaa tta gac aag ctt att tgg caa aca aga att acc aga gat caa aaa     624
Lys Leu Asp Lys Leu Ile Trp Gln Thr Arg Ile Thr Arg Asp Gln Lys
        195                 200                 205 gtt ctt aat gta aag agt ttt gaa gtt tat cat caa tta aat aaa gct     672
Val Leu Asn Val Lys Ser Phe Glu Val Tyr His Gln Leu Asn Lys Ala
    210                 215                 220 atc aca cat gca gta ggt gta caa tta aat cca act gta aca gtt gca     720
Ile Thr His Ala Val Gly Val Gln Leu Asn Pro Thr Val Thr Val Ala
225                 230                 235                 240 caa gtt gac caa gaa atc aaa gtg cta caa gaa gca tta aat act gct     768
```

```
Gln Val Asp Gln Glu Ile Lys Val Leu Gln Glu Ala Leu Asn Thr Ala
            245                 250                 255 cta cag taa                                                           777
Leu Gln <210> SEQ ID NO 2
<211> LENGTH: 258
<212> TYPE: PRT
<213> ORGANISM: Artificial Sequence
<220> FEATURE:
<223> OTHER INFORMATION: Description of Artificial Sequence: S. uberis
      CAMP factor

<400> SEQUENCE: 2

Met Leu Met Glu Phe Lys Lys Leu Leu Tyr Leu Thr Gly Ser Ile Ala
  1               5                  10                  15

Gly Ile Thr Leu Phe Ser Pro Ile Leu Thr Ser Val Gln Ala Asn Gln
             20                  25                  30

Ile Asn Val Ser Gln Pro Ser Asn Glu Ser Asn Val Ile Ser Gln
         35                  40                  45

Lys Lys Glu Glu Ile Asp Asn Ser Leu Asn Gln Glu Ser Ala Gln Leu
 50                  55                  60

Tyr Ala Leu Lys Glu Asp Val Lys Gly Thr Glu Lys Glu Gln Ser Val
 65                  70                  75                  80

Asn Ser Ala Ile Ser Ala Val Glu Asn Leu Lys Thr Ser Leu Arg Ala
                 85                  90                  95

Asn Pro Glu Thr Ile Tyr Asp Leu Asn Ser Ile Gly Thr Arg Val Glu
            100                 105                 110

Ala Ile Ser Asp Val Ile Gln Ala Ile Val Phe Ser Thr Gln Gln Leu
        115                 120                 125

Thr Asn Lys Val Asp Gln Ala His Ile Asp Met Gly Phe Ala Ile Thr
130                 135                 140

Lys Leu Leu Ile Arg Ile Ala Asp Pro Phe Ala Ser Asn Glu Ser Ile
145                 150                 155                 160

Lys Gly Gln Val Glu Ala Val Lys Gln Val Gln Ala Thr Val Leu Thr
                165                 170                 175

Tyr Pro Asp Leu Gln Pro Thr Asp Arg Ala Thr Ile Tyr Val Lys Ser
            180                 185                 190

Lys Leu Asp Lys Leu Ile Trp Gln Thr Arg Ile Thr Arg Asp Gln Lys
        195                 200                 205

Val Leu Asn Val Lys Ser Phe Glu Val Tyr His Gln Leu Asn Lys Ala
210                 215                 220

Ile Thr His Ala Val Gly Val Gln Leu Asn Pro Thr Val Thr Val Ala
225                 230                 235                 240

Gln Val Asp Gln Glu Ile Lys Val Leu Gln Glu Ala Leu Asn Thr Ala
            245                 250                 255

Leu Gln

<210> SEQ ID NO 3
<211> LENGTH: 768
<212> TYPE: DNA
<213> ORGANISM: Artificial Sequence
<220> FEATURE:
<223> OTHER INFORMATION: Description of Artificial Sequence: S.
      agalactiae CAMP factor
<220> FEATURE:
<221> NAME/KEY: CDS
<222> LOCATION: (1)..(768)
```

<400> SEQUENCE: 3

```
atg aac gtt aca cat atg atg tat cta tct gga act cta gtg gct ggt      48
Met Asn Val Thr His Met Met Tyr Leu Ser Gly Thr Leu Val Ala Gly
 1               5                  10                  15 gca ttg tta ttt tca cca gct gta tta gaa gta cat gct gat caa gtg      96
Ala Leu Leu Phe Ser Pro Ala Val Leu Glu Val His Ala Asp Gln Val
             20                  25                  30 aca act cca caa gtg gta aat cat gta aat agt aat aat caa gcc cag     144
Thr Thr Pro Gln Val Val Asn His Val Asn Ser Asn Asn Gln Ala Gln
         35                  40                  45 caa atg gct caa aag ctt gat caa gat agc att cag ttg aga aat atc     192
Gln Met Ala Gln Lys Leu Asp Gln Asp Ser Ile Gln Leu Arg Asn Ile
     50                  55                  60 aaa gat aat gtt cag gga aca gat tat gaa aaa ccg gtt aat gag gct     240
Lys Asp Asn Val Gln Gly Thr Asp Tyr Glu Lys Pro Val Asn Glu Ala
 65                  70                  75                  80 att act agc gtg gaa aaa tta aag act tca ttg cgt gcc aac cct gag     288
Ile Thr Ser Val Glu Lys Leu Lys Thr Ser Leu Arg Ala Asn Pro Glu
                 85                  90                  95 aca gtt tat gat ttg aat tct att ggt agt cgt gta gaa gcc tta aca     336
Thr Val Tyr Asp Leu Asn Ser Ile Gly Ser Arg Val Glu Ala Leu Thr
            100                 105                 110 gat gtg att gaa gca atc act ttt tca act caa cat tta aca aat aag     384
Asp Val Ile Glu Ala Ile Thr Phe Ser Thr Gln His Leu Thr Asn Lys
        115                 120                 125 gtt agt caa gca aat att gat atg gga ttt ggg ata act aag cta gtt     432
Val Ser Gln Ala Asn Ile Asp Met Gly Phe Gly Ile Thr Lys Leu Val
    130                 135                 140 att cgc att tta gat cca ttt gct tca gtt gat tca att aaa gct caa     480
Ile Arg Ile Leu Asp Pro Phe Ala Ser Val Asp Ser Ile Lys Ala Gln
145                 150                 155                 160 gtt aac gat gta aag gca tta gaa caa aaa gtt tta act tat cct gat     528
Val Asn Asp Val Lys Ala Leu Glu Gln Lys Val Leu Thr Tyr Pro Asp
                165                 170                 175 tta aaa cca act gat aga gct acc atc tat aca aaa tca aaa ctt gat     576
Leu Lys Pro Thr Asp Arg Ala Thr Ile Tyr Thr Lys Ser Lys Leu Asp
            180                 185                 190 aag gaa atc tgg aat aca cgc ttt act aga gat aaa aaa gta ctt aac     624
Lys Glu Ile Trp Asn Thr Arg Phe Thr Arg Asp Lys Lys Val Leu Asn
        195                 200                 205 gtc aaa gaa ttt aaa gtt tac aat act tta aat aaa gca atc aca cat     672
Val Lys Glu Phe Lys Val Tyr Asn Thr Leu Asn Lys Ala Ile Thr His
    210                 215                 220 gct gtt gga gtt cag ttg aat cca aat gtt acg gta caa caa gtt gat     720
Ala Val Gly Val Gln Leu Asn Pro Asn Val Thr Val Gln Gln Val Asp
225                 230                 235                 240 caa gag att gta aca tta caa gca gca ctt caa aca gca tta aaa taa     768
Gln Glu Ile Val Thr Leu Gln Ala Ala Leu Gln Thr Ala Leu Lys
                245                 250                 255
```

<210> SEQ ID NO 4
<211> LENGTH: 255
<212> TYPE: PRT
<213> ORGANISM: Artificial Sequence
<220> FEATURE:
<223> OTHER INFORMATION: Description of Artificial Sequence: S. agalactiae CAMP factor

<400> SEQUENCE: 4

```
Met Asn Val Thr His Met Met Tyr Leu Ser Gly Thr Leu Val Ala Gly
 1               5                  10                  15
```

```
Ala Leu Leu Phe Ser Pro Ala Val Leu Glu Val His Ala Asp Gln Val
            20                  25                  30

Thr Thr Pro Gln Val Val Asn His Val Asn Ser Asn Asn Gln Ala Gln
        35                  40                  45

Gln Met Ala Gln Lys Leu Asp Gln Asp Ser Ile Gln Leu Arg Asn Ile
    50                  55                  60

Lys Asp Asn Val Gln Gly Thr Asp Tyr Glu Lys Pro Val Asn Glu Ala
65                  70                  75                  80

Ile Thr Ser Val Glu Lys Leu Lys Thr Ser Leu Arg Ala Asn Pro Glu
                85                  90                  95

Thr Val Tyr Asp Leu Asn Ser Ile Gly Ser Arg Val Glu Ala Leu Thr
            100                 105                 110

Asp Val Ile Glu Ala Ile Thr Phe Ser Thr Gln His Leu Thr Asn Lys
        115                 120                 125

Val Ser Gln Ala Asn Ile Asp Met Gly Phe Gly Ile Thr Lys Leu Val
    130                 135                 140

Ile Arg Ile Leu Asp Pro Phe Ala Ser Val Asp Ser Ile Lys Ala Gln
145                 150                 155                 160

Val Asn Asp Val Lys Ala Leu Glu Gln Lys Val Leu Thr Tyr Pro Asp
                165                 170                 175

Leu Lys Pro Thr Asp Arg Ala Thr Ile Tyr Thr Lys Ser Lys Leu Asp
            180                 185                 190

Lys Glu Ile Trp Asn Thr Arg Phe Thr Arg Asp Lys Lys Val Leu Asn
        195                 200                 205

Val Lys Glu Phe Lys Val Tyr Asn Thr Leu Asn Lys Ala Ile Thr His
    210                 215                 220

Ala Val Gly Val Gln Leu Asn Pro Asn Val Thr Val Gln Asn Val Asp
225                 230                 235                 240

Gln Glu Ile Val Thr Leu Gln Ala Ala Leu Gln Thr Ala Leu Lys
                245                 250                 255

<210> SEQ ID NO 5
<211> LENGTH: 161
<212> TYPE: PRT
<213> ORGANISM: Artificial Sequence
<220> FEATURE:
<223> OTHER INFORMATION: Description of Artificial Sequence: consensus
      sequence

<400> SEQUENCE: 5

Met Tyr Leu Gly Ala Gly Leu Phe Ser Pro Val Ala Gln Gln Asn Leu
1               5                   10                  15

Gln Ser Gln Leu Lys Val Gly Thr Glu Val Asn Ala Ile Val Glu Leu
            20                  25                  30

Lys Thr Ser Leu Arg Ala Asn Pro Glu Thr Tyr Asp Leu Asn Ser Ile
        35                  40                  45

Gly Arg Val Glu Ala Asp Val Ile Ala Ile Phe Ser Thr Gln Leu Thr
    50                  55                  60

Asn Lys Val Gln Ala Ile Asp Met Gly Phe Ile Thr Lys Leu Ile Arg
65                  70                  75                  80

Ile Asp Pro Phe Ala Ser Ile Lys Gln Val Val Lys Val Leu Thr
                85                  90                  95

Tyr Pro Asp Leu Pro Thr Asp Arg Ala Thr Ile Tyr Lys Ser Lys Leu
            100                 105                 110

Asp Lys Ile Trp Thr Arg Thr Arg Asp Lys Val Leu Asn Val Lys Phe
```

-continued

```
            115                 120                 125
Val Tyr Leu Asn Lys Ala Ile Thr His Ala Val Gly Val Gln Leu Asn
        130                 135                 140

Pro Val Thr Val Gln Val Asp Gln Glu Ile Leu Gln Ala Leu Thr Ala
145                 150                 155                 160

Leu

<210> SEQ ID NO 6
<211> LENGTH: 31
<212> TYPE: PRT
<213> ORGANISM: Artificial Sequence
<220> FEATURE:
<223> OTHER INFORMATION: Description of Artificial Sequence: putative
      signal sequence of S. agalactiae CAMP factor

<400> SEQUENCE: 6

Met Asn Val Thr His Met Met Tyr Leu Ser Gly Thr Leu Val Ala Gly
  1               5                  10                  15

Ala Leu Leu Phe Ser Pro Ala Val Leu Glu Val His Ala Asp Gln
                20                  25                  30

<210> SEQ ID NO 7
<211> LENGTH: 32
<212> TYPE: PRT
<213> ORGANISM: Artificial Sequence
<220> FEATURE:
<223> OTHER INFORMATION: Description of Artificial Sequence: putative
      signal sequence of S. uberis CAMP factor

<400> SEQUENCE: 7

Met Leu Met Glu Phe Lys Lys Leu Leu Tyr Leu Thr Gly Ser Ile Ala
  1               5                  10                  15

Gly Ile Thr Leu Phe Ser Pro Ile Leu Thr Ser Val Gln Ala Asn Gln
                20                  25                  30

<210> SEQ ID NO 8
<211> LENGTH: 945
<212> TYPE: DNA
<213> ORGANISM: Artificial Sequence
<220> FEATURE:
<223> OTHER INFORMATION: Description of Artificial Sequence: LipoF:CAMP3
      chimera
<220> FEATURE:
<221> NAME/KEY: CDS
<222> LOCATION: (1)..(945)

<400> SEQUENCE: 8 atg aaa aaa ata aca ggg att att tta ttg ctt ctt gca gtc att att        48
Met Lys Lys Ile Thr Gly Ile Ile Leu Leu Leu Leu Ala Val Ile Ile
  1               5                  10                  15 ctg tct gca tgc cag gca aac tac gga tcc aat caa ata aat gtt agt        96
Leu Ser Ala Cys Gln Ala Asn Tyr Gly Ser Asn Gln Ile Asn Val Ser
                20                  25                  30 caa cca tct aat aat gaa agt aat gtt att tca cag aaa aaa gaa gaa       144
Gln Pro Ser Asn Asn Glu Ser Asn Val Ile Ser Gln Lys Lys Glu Glu
            35                  40                  45 att gat aat agt cta aat cag gaa agt gct caa cta tat gcc ttg aaa       192
Ile Asp Asn Ser Leu Asn Gln Glu Ser Ala Gln Leu Tyr Ala Leu Lys
        50                  55                  60 gaa gat gtt aaa gga act gag aaa gaa caa tca gtt aat tca gca att       240
Glu Asp Val Lys Gly Thr Glu Lys Glu Gln Ser Val Asn Ser Ala Ile
    65                  70                  75                  80 tca gct gtt gaa aat ctc gag caa gtg aca act cca caa gtg gta aat       288
```

```
                                                                              -continued Ser Ala Val Glu Asn Leu Glu Gln Val Thr Thr Pro Gln Val Val Asn
                 85                  90                  95 cat gta aat agt aat aat caa gcc cag caa atg gct caa aag ctt gat       336
His Val Asn Ser Asn Asn Gln Ala Gln Gln Met Ala Gln Lys Leu Asp
                100                 105                 110 caa gat agc att cag ttg aga aat atc aaa gat aat gtt cag gga aca       384
Gln Asp Ser Ile Gln Leu Arg Asn Ile Lys Asp Asn Val Gln Gly Thr
            115                 120                 125 gat tat gaa aaa ccg gtt aat gag gct att act agc gtg gaa aaa tta       432
Asp Tyr Glu Lys Pro Val Asn Glu Ala Ile Thr Ser Val Glu Lys Leu
        130                 135                 140 agg gct aaa act tca ctt aga gct aat cct gaa aca att tat gat tta       480
Arg Ala Lys Thr Ser Leu Arg Ala Asn Pro Glu Thr Ile Tyr Asp Leu
145                 150                 155                 160 aat tcg att gga aca aga gta gaa gca atc tct gac gtg att caa gca       528
Asn Ser Ile Gly Thr Arg Val Glu Ala Ile Ser Asp Val Ile Gln Ala
                165                 170                 175 att gtt ttt tca acg caa cag tta aca aat aaa gtt gat caa gct cac       576
Ile Val Phe Ser Thr Gln Gln Leu Thr Asn Lys Val Asp Gln Ala His
            180                 185                 190 att gat atg gga ttt gct att acg aaa tta ctt att cgc att gca gac       624
Ile Asp Met Gly Phe Ala Ile Thr Lys Leu Leu Ile Arg Ile Ala Asp
        195                 200                 205 cca ttt gct tca aat gaa tcc att aaa ggg caa gtc gaa gct gtt aaa       672
Pro Phe Ala Ser Asn Glu Ser Ile Lys Gly Gln Val Glu Ala Val Lys
    210                 215                 220 caa gtg caa gcg act gtg ctt acc tat ccc gat ttg cag cct acg gat       720
Gln Val Gln Ala Thr Val Leu Thr Tyr Pro Asp Leu Gln Pro Thr Asp
225                 230                 235                 240 aga gca act att tac gtt aaa tca aaa tta gac aag ctt att tgg caa       768
Arg Ala Thr Ile Tyr Val Lys Ser Lys Leu Asp Lys Leu Ile Trp Gln
                245                 250                 255 aca aga att acc aga gat caa aaa gtt ctt aat gta aag agt ttt gaa       816
Thr Arg Ile Thr Arg Asp Gln Lys Val Leu Asn Val Lys Ser Phe Glu
            260                 265                 270 gtt tat cat caa tta aat aaa gct atc aca cat gca gta ggt gta caa       864
Val Tyr His Gln Leu Asn Lys Ala Ile Thr His Ala Val Gly Val Gln
        275                 280                 285 tta aat cca act gta aca gtt gca caa gtt gac caa gaa atc aaa gtg       912
Leu Asn Pro Thr Val Thr Val Ala Gln Val Asp Gln Glu Ile Lys Val
    290                 295                 300 cta caa gaa gca tta aat act gct cta cag taa                           945
Leu Gln Glu Ala Leu Asn Thr Ala Leu Gln
305                 310                 315

<210> SEQ ID NO 9
<211> LENGTH: 314
<212> TYPE: PRT
<213> ORGANISM: Artificial Sequence
<220> FEATURE:
<223> OTHER INFORMATION: Description of Artificial Sequence: LipoF:CAMP3
      chimera

<400> SEQUENCE: 9

Met Lys Lys Ile Thr Gly Ile Ile Leu Leu Leu Leu Ala Val Ile Ile
1               5                   10                  15

Leu Ser Ala Cys Gln Ala Asn Tyr Gly Ser Asn Gln Ile Asn Val Ser
                20                  25                  30

Gln Pro Ser Asn Asn Glu Ser Asn Val Ile Ser Gln Lys Lys Glu Glu
            35                  40                  45
```

```
Ile Asp Asn Ser Leu Asn Gln Glu Ser Ala Gln Leu Tyr Ala Leu Lys
 50                  55                  60

Glu Asp Val Lys Gly Thr Glu Lys Glu Gln Ser Val Asn Ser Ala Ile
 65                  70                  75                  80

Ser Ala Val Glu Asn Leu Glu Gln Val Thr Thr Pro Gln Val Val Asn
                 85                  90                  95

His Val Asn Ser Asn Asn Gln Ala Gln Gln Met Ala Gln Lys Leu Asp
                100                 105                 110

Gln Asp Ser Ile Gln Leu Arg Asn Ile Lys Asp Asn Val Gln Gly Thr
                115                 120                 125

Asp Tyr Glu Lys Pro Val Asn Glu Ala Ile Thr Ser Val Glu Lys Leu
130                 135                 140

Arg Ala Lys Thr Ser Leu Arg Ala Asn Pro Glu Thr Ile Tyr Asp Leu
145                 150                 155                 160

Asn Ser Ile Gly Thr Arg Val Glu Ala Ile Ser Asp Val Ile Gln Ala
                165                 170                 175

Ile Val Phe Ser Thr Gln Gln Leu Thr Asn Lys Val Asp Gln Ala His
                180                 185                 190

Ile Asp Met Gly Phe Ala Ile Thr Lys Leu Leu Ile Arg Ile Ala Asp
                195                 200                 205

Pro Phe Ala Ser Asn Glu Ser Ile Lys Gly Gln Val Glu Ala Val Lys
210                 215                 220

Gln Val Gln Ala Thr Val Leu Thr Tyr Pro Asp Leu Gln Pro Thr Asp
225                 230                 235                 240

Arg Ala Thr Ile Tyr Val Lys Ser Lys Leu Asp Lys Leu Ile Trp Gln
                245                 250                 255

Thr Arg Ile Thr Arg Asp Gln Lys Val Leu Asn Val Lys Ser Phe Glu
                260                 265                 270

Val Tyr His Gln Leu Asn Lys Ala Ile Thr His Ala Val Gly Val Gln
                275                 280                 285

Leu Asn Pro Thr Val Thr Val Ala Gln Val Asp Gln Glu Ile Lys Val
290                 295                 300

Leu Gln Glu Ala Leu Asn Thr Ala Leu Gln
305                 310

<210> SEQ ID NO 10
<211> LENGTH: 36
<212> TYPE: DNA
<213> ORGANISM: Artificial Sequence
<220> FEATURE:
<223> OTHER INFORMATION: Description of Artificial Sequence: CAMP-1

<400> SEQUENCE: 10
aaaaaaggat ccaatcaaat aaatgttagt caacca                                36

<210> SEQ ID NO 11
<211> LENGTH: 49
<212> TYPE: DNA
<213> ORGANISM: Artificial Sequence
<220> FEATURE:
<223> OTHER INFORMATION: Description of Artificial Sequence: CAMP-2

<400> SEQUENCE: 11
aaaaaccatg gctactcgag attttcaaca gctgaattgc tgaattaac                  49

<210> SEQ ID NO 12
<211> LENGTH: 34
<212> TYPE: DNA
```

```
<213> ORGANISM: Artificial Sequence
<220> FEATURE:
<223> OTHER INFORMATION: Description of Artificial Sequence: CAMP-3

<400> SEQUENCE: 12
aaaaaactcg agcaagtgac aactccacaa gtgg                           34

<210> SEQ ID NO 13
<211> LENGTH: 48
<212> TYPE: DNA
<213> ORGANISM: Artificial Sequence
<220> FEATURE:
<223> OTHER INFORMATION: Description of Artificial Sequence: CAMP-4

<400> SEQUENCE: 13
aaaaaaccat ggctaaggcc ttaattttc cacgctagta atagcctc             48

<210> SEQ ID NO 14
<211> LENGTH: 36
<212> TYPE: DNA
<213> ORGANISM: Artificial Sequence
<220> FEATURE:
<223> OTHER INFORMATION: Description of Artificial Sequence: CAMP-5

<400> SEQUENCE: 14
aaaaaagcgc taaaacttca cttagagcta atcctg                         36

<210> SEQ ID NO 15
<211> LENGTH: 41
<212> TYPE: DNA
<213> ORGANISM: Artificial Sequence
<220> FEATURE:
<223> OTHER INFORMATION: Description of Artificial Sequence: CAMP-6

<400> SEQUENCE: 15
aaaaaccatg gtcattactg tagagcagta tttaatgctt c                   41

<210> SEQ ID NO 16
<211> LENGTH: 38
<212> TYPE: DNA
<213> ORGANISM: Artificial Sequence
<220> FEATURE:
<223> OTHER INFORMATION: Description of Artificial Sequence: His-CAMP-1

<400> SEQUENCE: 16
aaaaaacata tgtccaatca aataaatgtt agtcaacc                       38

<210> SEQ ID NO 17
<211> LENGTH: 35
<212> TYPE: DNA
<213> ORGANISM: Artificial Sequence
<220> FEATURE:
<223> OTHER INFORMATION: Description of Artificial Sequence: His-CAMP-2

<400> SEQUENCE: 17
tttttggatc cttactgtag agcagtattt aatgc                          35

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: 556-1

<400> SEQUENCE: 18
gtgtggaatt gtgagcgg                                             18
```

```
<210> SEQ ID NO 19
<211> LENGTH: 15
<212> TYPE: DNA
<213> ORGANISM: Artificial Sequence
<220> FEATURE:
<223> OTHER INFORMATION: Description of Artificial Sequence: 556-2

<400> SEQUENCE: 19
ctccctgcct ctgtc                                               15
```